(12) United States Patent
Tai et al.

(10) Patent No.: US 8,906,623 B2
(45) Date of Patent: Dec. 9, 2014

(54) KIT AND METHOD FOR DETERMINING WHETHER OR NOT UNMETHYLATED CYTOSINE CONVERSION TREATMENT IS PROPERLY CARRIED OUT AND METHOD FOR ANALYZING METHYLATED DNA USING THE SAME

(75) Inventors: Kaya Tai, Kobe (JP); Ayako Sakai, Kobe (JP); Noriaki Yamamoto, Kobe (JP); Noriko Oka, Kobe (JP); Masahiro Kajita, Kobe (JP)

(73) Assignee: Sysmex Corporation, Hyogo (JP)

( * ) Notice: Subject to any disclaimer, the term of this patent is extended or adjusted under 35 U.S.C. 154(b) by 646 days.

(21) Appl. No.: 12/935,846

(22) PCT Filed: Mar. 16, 2009

(86) PCT No.: PCT/JP2009/055080
§ 371 (c)(1),
(2), (4) Date: Sep. 30, 2010

(87) PCT Pub. No.: WO2009/122892
PCT Pub. Date: Oct. 8, 2009

(65) Prior Publication Data
US 2011/0027799 A1   Feb. 3, 2011

(30) Foreign Application Priority Data
Mar. 31, 2008   (JP) .................................. 2008-090644

(51) Int. Cl.
*C12Q 1/68*   (2006.01)
*C12P 19/34*   (2006.01)

(52) U.S. Cl.
CPC .................................. *C12Q 1/6827* (2013.01)
USPC ......................................... 435/6.12; 435/91.2

(58) Field of Classification Search
None
See application file for complete search history.

(56) References Cited

U.S. PATENT DOCUMENTS

2009/0123923 A1*  5/2009  Yamamoto et al. ............... 435/6

FOREIGN PATENT DOCUMENTS

| EP | 1930446 A2 | 6/2008 |
|---|---|---|
| JP | 2005-058217 | 3/2005 |
| WO | WO 2007/039101 A1 | 4/2007 |

OTHER PUBLICATIONS

Masahiro Sasaki, et al., "Bisulfite conversion-specific and methylation-specific PCR: a sensitive technique for accurate evaluation of CpG methylation", Biochemical and Biophysical Research Communications, 2003, pp. 305-309, vol. 309.
Sho Koda, et al. "Bisulfite Shori ni yoru DNA Methyl-kano Kenshutsuho", Experimental Medicine, 2006, pp. 1793-1797, vol. 24, No. 12.
Zhenggang Xiong, et al., "COBRA: a sensitive and quantitative DNA methylation assay", Nucleic Acids Research, 1997, pp. 2532-2534, vol. 25, No. 12.
Keith Rand, "Conversion-specific detection of DNA methylation using real-time polymerase chain reaction (ConLight-MSP) to avoid false positives", Methods, 2002, pp. 114-120, vol. 27.
C. Grunau et al., "Bisulfite genomic sequencing: systematic investigation of critical experimental parameters", Nucleic Acids Research, 2001, 29(13): 1-7.
European Search Report issued in corresponding EP Application No. 09727922.8 on Nov. 22, 2011 (in the name of Sysmex Corporation).
Naoyuki Umetani et al., "Methylation of p16 and Ras Association Domain Family Protein 1a during Colorectal Malignant Transformation", Mol. Cancer Research, 2006, 4(5): 303-309.
Grunau et al., "MethDB—a public database for DNA methylation data", Nucleic Acids Research, 29(1):270-274 (2001).
Japanese Office Action issued in corresponding Japanese Application No. 2010-505545.

\* cited by examiner

*Primary Examiner* — Kenneth R. Horlick
*Assistant Examiner* — David Thomas
(74) *Attorney, Agent, or Firm* — Sughrue Mion, PLLC

(57) ABSTRACT

Success or failure of unmethylated cytosine conversion treatment is determined by using a first primer set comprising plural primers that hybridize with a nucleic acid comprising a nucleotide sequence not containing cytosine in the nucleotide sequence of biological DNA that is subject to an unmethylated cytosine conversion treatment and a second primer set comprising plural primers that hybridize with a nucleic acid comprising a nucleotide sequence in which cytosine in a nucleotide sequence containing cytosine and not containing a CpG site is converted into a base other than cytosine, in the nucleotide sequence of biological DNA.

15 Claims, 7 Drawing Sheets

```
                        SEQUENCE LISTING

<160> NUMBER OF SEQ ID NOS: 10

<210> SEQ ID NO 1
<211> LENGTH: 30
<212> TYPE: DNA
<213> ORGANISM: Artificial
<220> FEATURE:
<223> OTHER INFORMATION: A sequence of a primer

<400> SEQUENCE: 1
agggagtaga gaaaaagtag gaagatgagt                                    30

<210> SEQ ID NO 2
<211> LENGTH: 21
<212> TYPE: DNA
<213> ORGANISM: Artificial
<220> FEATURE:
<223> OTHER INFORMATION: A sequence if a primer

<400> SEQUENCE: 2
tccaacatca catccaatcc a                                             21

<210> SEQ ID NO 3
<211> LENGTH: 27
<212> TYPE: DNA
<213> ORGANISM: Artificial
<220> FEATURE:
<223> OTHER INFORMATION: A sequence of a primer

<400> SEQUENCE: 3
aaaaagtagg aagatgagtt agaaggt                                       27

<210> SEQ ID NO 4
<211> LENGTH: 19
<212> TYPE: DNA
<213> ORGANISM: Artificial
<220> FEATURE:
<223> OTHER INFORMATION: A sequence of a primer

<400> SEQUENCE: 4
ccaccaccca tatctcaaa                                                19

<210> SEQ ID NO 5
<211> LENGTH: 33
<212> TYPE: DNA
<213> ORGANISM: Artificial
<220> FEATURE:
<223> OTHER INFORMATION: A sequence of a primer

<400> SEQUENCE: 5
gggatattaa gtggagttat tttggtttta gtt                                33
```

```
<210> SEQ ID NO 6
<211> LENGTH: 20
<212> TYPE: DNA
<213> ORGANISM: Artificial
<220> FEATURE:
<223> OTHER INFORMATION: A sequence of a primer

<400> SEQUENCE: 6
ccctcccaac atccttccta                                              20

<210> SEQ ID NO 7
<211> LENGTH: 224
<212> TYPE: DNA
<213> ORGANISM: Artificial
<220> FEATURE:
<223> OTHER INFORMATION: A target sequence

<400> SEQUENCE: 7
gttgtttttt agaataggga gtagagaaaa agtaggaaga tgagttagaa ggctatcatt   60
gggatgtgta agagatgaag gagagtttag attagggtga taatgagtgt gttgggaaat  120
agacgaagat agaatagtgg attggatgtg atgttggaga aattggatat atgatggatt  180
tgtttcctga gatatgggtg gtggttggag agtaattgga agag                   224

<210> SEQ ID NO 8
<211> LENGTH: 109
<212> TYPE: DNA
<213> ORGANISM: Artificial
<220> FEATURE:
<223> OTHER INFORMATION: A sequence of a standard DNA

<400> SEQUENCE: 8
agggagtaga gaaaaagtag gaagatgagt tagaaggtta gggtgataat gagtgtgttg   60
ggaaatagat tgagatatg ggtggtggtg gattggatgt gatgttgga                109

<210> SEQ ID NO 9
<211> LENGTH: 143
<212> TYPE: DNA
<213> ORGANISM: Artificial
<220> FEATURE:
<223> OTHER INFORMATION: A sequence of a standard DNA corresponding
      primer set 1 for determining an amount of a nucleic acid

<400> SEQUENCE: 9
agggagtaga gaaaaagtag gaagatgagt tagaaggcta tcattgggat gtgtaagaga   60
tgaaggagag tttagaccag ggtgataatg agtgtgttgg gaaatagacg aagatagaac  120
agtggattgg atgtgatgtt gga                                          143

<210> SEQ ID NO 10
<211> LENGTH: 127
<212> TYPE: DNA
<213> ORGANISM: Artificial
<220> FEATURE:
<223> OTHER INFORMATION: A sequence of a standard DNA corresponding
      primer set 1 for checking a conversion treatment

<400> SEQUENCE: 10
gggatattaa gtggagttat tttggtttta tgaggagggt ttattttttg ggaagaggac   60
ggagtggttt gtttaggcgc gtggagagtc ggcgagggtt aggggtttag gaaggatgtt  120
gggaggg                                                            127
```

US 8,906,623 B2

KIT AND METHOD FOR DETERMINING WHETHER OR NOT UNMETHYLATED CYTOSINE CONVERSION TREATMENT IS PROPERLY CARRIED OUT AND METHOD FOR ANALYZING METHYLATED DNA USING THE SAME

TECHNICAL FIELD

The present invention relates to a kit and method for determining whether or not an unmethylated cytosine conversion treatment is properly carried out and a method for analyzing methylated DNA using the same.

BACKGROUND ART

In chromosomal DNA of a higher eukaryote such as human, cytosine in a CpG site comprising a CG dinucleotide sequence is methylated in some cases. This methylation of cytosine in a CpG site functions as a mechanism for suppressing expression of genes. For example, a region containing a large amount of CpG sites is present in a promoter region of a gene, and on-off of transcription from DNA of the gene is controlled by the presence or absence of methylation of cytosine in this promoter region of a gene.

Control of gene expression by DNA methylation plays an important role in events such as early embryo development, tissue-specific gene expression, gene imprinting, inactivation of X chromosome, stabilization of chromosome, and typing of DNA replication. In addition, it has been reported that DNA methylation may be highly involved in diseases such as cancer.

As a method for analyzing DNA methylation described above, methylation-specific PCR method or bisulfite sequencing method is generally used. In these methods, a treatment of converting cytosine that is not methylated (unmethylated cytosine) in DNA to be analyzed into another base (unmethylated cytosine conversion treatment) is carried out by using bisulfite that is a reagent for converting unmethylated cytosine into another base (unmethylated cytosine conversion agent). In the Methylation-specific PCR method, DNA methylation is analyzed by carrying out a polymerase chain reaction of each of a primer set in the case where cytosine is converted into another base and a primer set in the case where cytosine is not converted into another base using DNA after the unmethylated cytosine conversion treatment and examining the presence or absence of amplification product. In addition, in the bisulfite sequencing method, DNA methylation is analyzed by determining a nucleotide sequence of DNA after the unmethylated cytosine conversion treatment.

Therefore, by the methylation-specific PCR method and the bisulfite sequencing method, methylated DNA cannot be accurately detected unless an unmethylated cytosine conversion treatment is properly carried out. Therefore, determination of whether or not an unmethylated cytosine conversion treatment is properly carried out is required to carry out the accurate detection of methylated DNA.

Incidentally, Patent Publication 1 discloses, as a primer for confirmation of whether or not bisulfite treatment is properly carried out, a primer that is designed based on a region not containing a CG sequence and has a nucleotide sequence in which cytosine is converted into thymine in the nucleotide sequence.

[Patent Publication 1] Japanese Patent Laid-Open No. 2005-58217

DISCLOSURE OF THE INVENTION

An object of the present invention is to provide a kit and method, which can accurately determine whether or not an unmethylated cytosine conversion treatment is properly carried out. In addition, another object of the present invention is to provide a method for analyzing methylated DNA, which can analyze accurately and efficiently methylated DNA.

More specifically, the present invention relates to:
(1) a kit for determining whether or not an unmethylated cytosine conversion treatment that converts unmethylated cytosine into a base other than cytosine is properly carried out, comprising:
a first primer set comprising plural primers that hybridize with a nucleic acid comprising a nucleotide sequence not containing cytosine in the nucleotide sequence of biological DNA that is subject to an unmethylated cytosine conversion treatment and
a second primer set comprising plural primers that hybridize with a nucleic acid comprising a nucleotide sequence in which cytosine in a nucleotide sequence containing cytosine and not containing a CpG site is converted into a base other than cytosine, in the nucleotide sequence of biological DNA,
(2) the kit according to the above (1), wherein the nucleotide sequence not containing cytosine and the nucleotide sequence containing cytosine and not containing a CpG site are present in the same chromosome of the biological body,
(3) the kit according to the above (2), wherein the nucleotide sequence not containing cytosine and the nucleotide sequence containing cytosine and not containing a CpG site are contained in the nucleotide sequence of 300 bp or less in the nucleotide sequence of biological DNA,
(4) the kit according to the above (2) or (3), wherein at least one primer contained in the first primer set is a primer that hybridizes with a nucleic acid amplified by nucleic acid amplification using the second primer set,
(5) the kit according to the above (2) or (3), wherein at least one primer contained in the second primer set is a primer that hybridizes with a nucleic acid comprising a nucleotide sequence in which cytosine in a nucleic acid amplified by nucleic acid amplification using the first primer set is converted into a base other than cytosine,
(6) the kit according to the above (1), wherein the unmethylated cytosine conversion treatment is a treatment of DNA with bisulfite,
(7) the kit according to the above (1), wherein the base other than cytosine is uracil,
(8) the kit according to the above (1), wherein the biological DNA is human genomic DNA,
(9) the kit according to the above (1), wherein the biological DNA contains tumor cell DNA,
(10) the kit according to the above (1), wherein the first primer set is a primer set comprising a primer comprising a nucleotide sequence as shown in SEQ ID NO: 1 and a primer comprising a nucleotide sequence as shown in SEQ ID NO: 2,
(11) the kit according to the above (1), wherein the second primer set is a primer set comprising a primer comprising a nucleotide sequence as shown in SEQ ID NO: 3 and a primer comprising a nucleotide sequence as shown in SEQ ID NO: 4,
(12) a method for determining whether or not an unmethylated cytosine conversion treatment that converts unmethylated cytosine into a base other than cytosine is properly carried out, comprising the steps of:

(A) converting unmethylated cytosine of biological DNA contained in a sample into a base other than cytosine, to give an unmethylated cytosine conversion sample;
(B) carrying out nucleic acid amplification reactions of the following (i) and (ii):
   (i) a nucleic acid amplification reaction using the unmethylated cytosine conversion sample obtained in the step (A) and the first primer set comprising plural primers that hybridize with a nucleic acid comprising a nucleotide sequence not containing cytosine in the nucleotide sequence of the biological DNA and
   (ii) a nucleic acid amplification reaction using the unmethylated cytosine conversion sample obtained in the step (A) and the second primer set comprising plural primers that hybridize with a nucleic acid comprising a nucleotide sequence in which cytosine in a nucleotide sequence containing cytosine and not containing a CpG site is converted into a base other than cytosine in the nucleotide sequence of the biological DNA;
(C) determining the amount of the amplification product obtained in the nucleic acid amplification reaction (i) and the amount of the amplification product obtained in the nucleic acid amplification reaction (ii) of the step (B);
(D) calculating the ratio of the nucleic acid in which the unmethylated cytosine of the biological DNA is converted into a base other than cytosine in total nucleic acids contained in the unmethylated cytosine conversion sample obtained in the step (A), based on the determination result obtained in the step (C); and
(E) determining whether or not the step (A) is properly carried out, based on the calculation result obtained in the step (D), and
(13) a method for analyzing methylated DNA comprising the steps of:
(A) converting unmethylated cytosine of biological DNA contained in a sample into a base other than cytosine, to give an unmethylated cytosine conversion sample;
(B) carrying out nucleic acid amplification reactions of the following (i) and (ii):
   (i) a nucleic acid amplification reaction using the unmethylated cytosine conversion sample obtained in the step (A) and the first primer set comprising plural primers that hybridize with a nucleic acid comprising a nucleotide sequence not containing cytosine in the nucleotide sequence of the biological DNA and
   (ii) a nucleic acid amplification reaction using the unmethylated cytosine conversion sample obtained in the step (A) and the second primer set comprising plural primers that hybridize with a nucleic acid comprising a nucleotide sequence in which cytosine in a nucleotide sequence containing cytosine and not containing a CpG site is converted into a base other than cytosine in the nucleotide sequence of the biological DNA;
(C) determining the amount of the amplification product obtained in the nucleic acid amplification reaction (i) and the amount of the amplification product obtained in the nucleic acid amplification reaction (ii) of the step (B);
(D) calculating the ratio of the nucleic acid in which the unmethylated cytosine of the biological DNA is converted into a base other than cytosine in total nucleic acids contained in the unmethylated cytosine conversion sample obtained in the step (A), based on the determination result obtained in the step (C);
(E) determining whether or not the step (A) is properly carried out, based on the calculation result obtained in the step (D), and
(F) analyzing methylated DNA using the unmethylated cytosine conversion sample obtained in the step (A), when the step (A) is determined as properly carried out in the step (E).

BRIEF DESCRIPTION OF THE DRAWINGS

FIG. 4 (B) is a schematic diagram showing a binding region of each primer in primer set 1 for checking an amount of a nucleic acid and primer set 2 for checking a conversion treatment in a nucleotide sequence as shown in SEQ ID NO: 8.

BEST MODE FOR CARRYING OUT THE INVENTION

Figure 1:
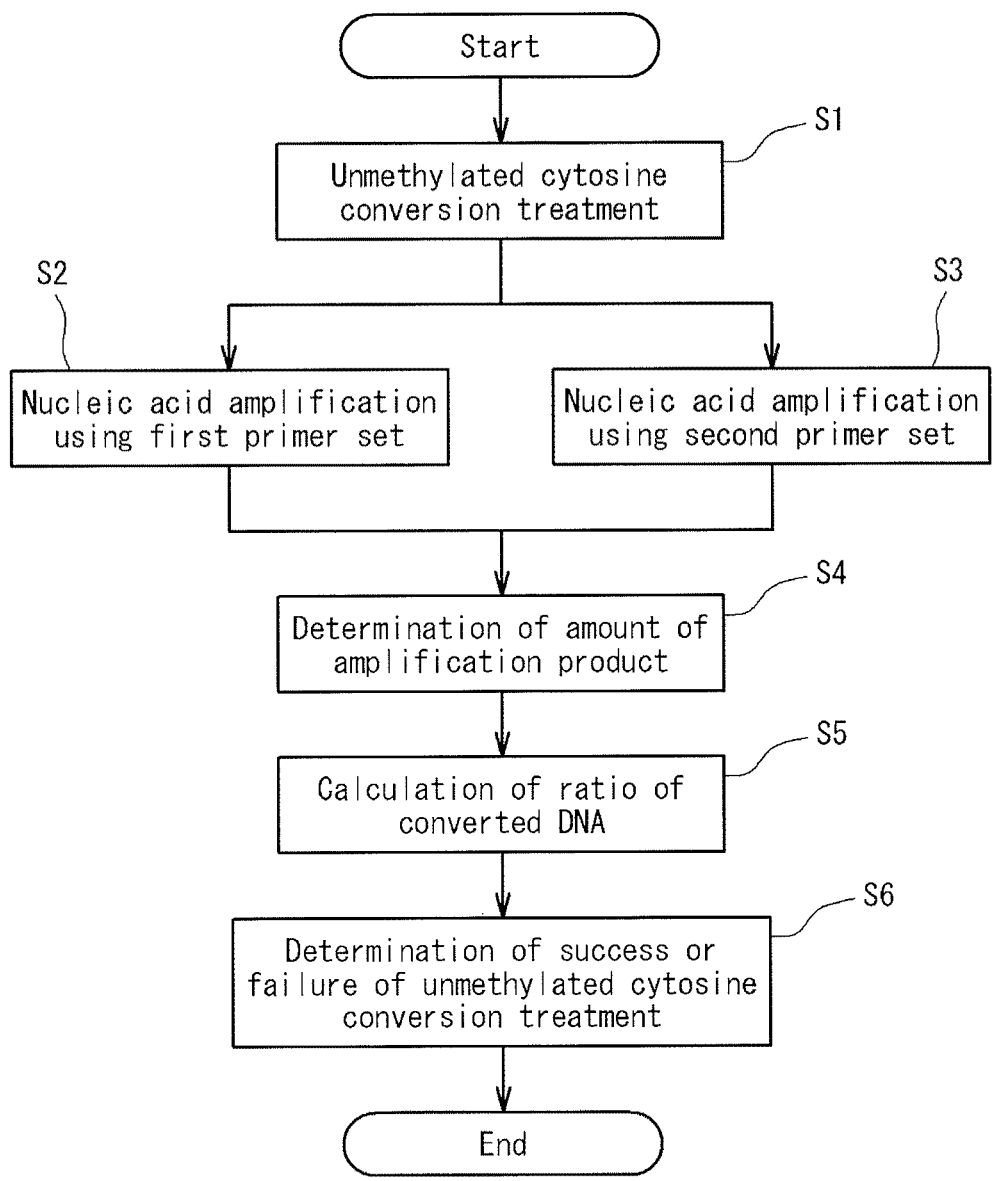
FIG. 1 is a flow chart showing one embodiment of the determination method of the present invention.

The present invention relates to, in one aspect, a kit for determining whether or not an unmethylated cytosine conversion treatment that converts unmethylated cytosine into a base other than cytosine is properly carried out, comprising a first primer set comprising plural primers that hybridize with a nucleic acid comprising a nucleotide sequence not containing cytosine in the nucleotide sequence of biological DNA that is subject to an unmethylated cytosine conversion treatment and a second primer set comprising plural primers that hybridize with a nucleic acid comprising a nucleotide sequence in which cytosine in a nucleotide sequence containing cytosine and not containing a CpG site is converted into a base other than cytosine, in the nucleotide sequence of biological DNA.

The kit of the present invention comprises the first primer set and the second primer set. The first primer set is a primer set that can accurately determine the information about the amount of total nucleic acids in an unmethylated cytosine conversion sample without substantially being affected by an unmethylated cytosine conversion treatment. In addition, the second primer set is a primer set that can accurately determine the information about the amount of a nucleic acid in which unmethylated cytosine is converted into a base other than cytosine by the unmethylated cytosine conversion treatment among total nucleic acids in the unmethylated cytosine conversion sample. Therefore, since by the kit of the present invention, the ratio of the nucleic acid in which unmethylated cytosine is converted into a base other than cytosine contained in total nucleic acids can be accurately determined, the kit exhibits an excellent effect that whether or not the unmethylated cytosine conversion treatment is properly carried out can be accurately determined.

As used herein, the "methylated cytosine" refers to cytosine in which 5-position of cytosine is methylated. In addition, "unmethylated cytosine" refers to cytosine in which 5-position of cytosine is not methylated.

As used herein, a base other than cytosine includes, for example, uracil, thymine, adenine, guanine, and the like. When an unmethylated cytosine conversion treatment is carried out by using bisulfite set forth below, the base other than cytosine is uracil.

As used herein, the "unmethylated cytosine conversion treatment" means a treatment that converts unmethylated cytosine contained in DNA into a base other than cytosine. In addition, the unmethylated cytosine conversion treatment is carried out by bringing an unmethylated cytosine conversion agent that converts unmethylated cytosine into a base other than cytosine into contact with DNA. Hereinafter, the nucleic acid in which unmethylated cytosine is converted into a base other than cytosine by the unmethylated cytosine conversion treatment is also referred to as a converted nucleic acid.

As used herein, the "unmethylated cytosine conversion sample" means a sample obtained by the unmethylated cytosine conversion treatment. The unmethylated cytosine conversion agent is not particularly limited as long as the unmethylated cytosine conversion agent is an agent that converts unmethylated cytosine into a base other than cytosine. For example, the unmethylated cytosine conversion agent includes bisulfite and the like. The bisulfite includes, for example, sodium hydrogen sulfite, potassium hydrogen sulfite, and the like. When the bisulfite is used as the unmethylated cytosine conversion agent, unmethylated cytosine is converted into uracil.

As used herein, the biological DNA is not particularly limited as long as it is DNA prepared from a biological body. The biological DNA can be prepared from blood, lymphocyte, urine, a tissue collected from biopsy and the like. In the present invention, the biological DNA is preferably human genomic DNA, and particularly preferably tumor cell DNA. Aberrant DNA methylation is frequently observed in the tumor cell DNA. When the kit of the present invention is used for the detection of the aberrant DNA methylation by the unmethylated cytosine conversion treatment, it can be confirmed that the unmethylated cytosine conversion treatment is properly carried out. Therefore, methylated DNA of the tumor cell DNA can be more accurately analyzed.

As used herein, "hybridize" means that a primer hybridizes with a nucleic acid under stringent conditions. The state where a primer hybridizes with a nucleic acid is a state where a primer and a nucleic acid are annealed in a nucleotide sequence complementary to each other. A primer hybridizes with a nucleic acid, thereby being the state suitable to promote a nucleic acid amplification reaction. Herein, "stringent conditions" refer to the conditions that are generally used by those skilled in the art when hybridization of polynucleotides, i.e., hybridization of a primer with a target nucleic acid, is carried out. More specifically, the conditions are not particularly limited as long as the conditions are conditions where both of the first primer and the second primer can hybridize with biological DNA after the unmethylated cytosine conversion treatment. The stringency in hybridization is known to be functions of the temperature, the salt concentration, the chain length of a primer, the GC content of nucleotide sequence of primers, and the concentration of a chaotropic agent in a hybridization buffer. As the stringent conditions, for example, the conditions described in Sambrook, J. et al. (1998) Molecular Cloning: A Laboratory Manual (2nd ed.), Cold Spring Harbor Laboratory Press, New York, and the like can be used.

The first primer set and the second primer set are primer sets for amplifying nucleic acid by a nucleic acid amplification reaction. The nucleic acid amplification reaction can be carried out by a nucleic acid amplification method. This nucleic acid amplification method is not particularly limited as long as the method is a method that can quantitatively determine the amount of an amplification product. The above nucleic acid amplification method includes, for example, a polymerase chain reaction (PCR) method, a strand displacement reaction method, a ligase chain reaction (LCR) method, a transcription amplification method, and the like. The PCR method can be carried out by the conventional method. The strand displacement reaction method includes, for example, the LAMP method, the ICAN (registered trademark) method, the SMAP method, and the like. The transcription amplification method includes, for example, the TAS method and the like. Incidentally, in the nucleic acid amplification reaction using the first primer set and the nucleic acid amplification reaction using the second primer set, uracil generated by the unmethylated cytosine conversion treatment with bisulfite is converted into thymine.

The first primer set and the second primer set can be designed by the known method depending on the type of nucleic acid amplification method to be used. For example, each primer set can be easily designed by entering the conditions of each primer set described below into a commercially available software for designing a primer. The software for designing a primer set used for a real-time PCR method that is a quantitative PCR method includes, for example, GENETYX, primer3, and the like. In addition, the software for designing a primer set used for the LAMP method that is a strand displacement reaction method includes, for example, Primer Explorer, and the like. A primer in each primer set can be obtained by synthesizing an oligonucleotide comprising the designed nucleotide sequence by the known method. Incidentally, the number of primers constituting each primer set varies depending on the type of nucleic acid amplification method to be used. For example, by the polymerase chain reaction method, each primer set each comprises two primers. In the LAMP method, each primer set each comprises at least four primers.

When the primer set is a primer set used in the PCR method, it is desirable that the difference in Tm value between a forward primer and a reverse primer is preferably 2° C. or less. In addition, it is desirable that the GC content of nucleotide sequence of each primer in the primer set is preferably from 40 to 60%. It is desirable that 4 or more consecutive guanines are not contained in the nucleotide sequence of one primer in the primer set. It is desirable that each primer in the primer set is 10 to 40 nucleotides in length and particularly preferably 15 to 35 nucleotides in length. Incidentally, when the PCR method is carried out by using this primer set, it is desirable that the annealing temperature during PCR is set at a temperature near Tm of each primer in the primer set.

The first primer set in the present invention comprises plural primers that hybridize with a nucleic acid comprising a nucleotide sequence not containing cytosine in the nucleotide sequence of biological DNA that is subject to an unmethylated cytosine conversion treatment. In the nucleic acid comprising the nucleotide sequence not containing cytosine, cytosine to be converted by the unmethylated cytosine conversion treatment is not present, so that the nucleotide sequence is not converted. Therefore, the primer contained in the first primer set can hybridize with the nucleic acid without substantially being affected by the unmethylated cytosine conversion treatment. Accordingly, using the nucleic acid contained in an unmethylated cytosine conversion sample as a template, the amount of the amplification product obtained by the nucleic acid amplification reaction using the first primer set can be determined to obtain the accurate information about the amount of total nucleic acids contained in the unmethylated cytosine conversion sample. Incidentally, the concrete first primer set in the case where human genomic DNA is used as the biological DNA includes, for example, a primer set comprising a primer comprising a nucleotide sequence as shown in SEQ ID NO: 1 and a primer comprising a nucleotide sequence as shown in SEQ ID NO: 2, and the like.

The second primer set in the present invention comprises plural primers that hybridize with a nucleic acid comprising a nucleotide sequence in which cytosine in a nucleotide sequence containing cytosine and not containing a CpG site is converted into a base other than cytosine, in the nucleotide sequence of the biological DNA. As described above, since the methylation of cytosine occurs at the cytosine in a CpG site, the nucleotide sequence containing cytosine and not containing a CpG site does not contain methylated cytosine in the biological DNA. Therefore, in the biological DNA comprising the nucleotide sequence containing cytosine and not containing a CpG site, all cytosines are converted into bases other than cytosine by an unmethylated cytosine conversion treatment, and thus the nucleotide sequence is converted. Accordingly, the primer contained in the second primer set can complementarily hybridize with a nucleic acid in which cytosine of the biological DNA that is the subject of hybridization is converted into a base other than cytosine by an unmethylated cytosine conversion treatment. However, in a nucleic acid in which the cytosine of the biological DNA that is the subject of hybridization is not converted into a base other than cytosine, the primer contained in the second primer set cannot complementarily hybridize with a moiety where cytosine is not converted into a base other than cytosine. As a result, in the case where the cytosine of the biological DNA that is the subject of hybridization is converted into a base other than cytosine by an unmethylated cytosine conversion treatment, an amplification product is efficiently produced by a nucleic acid amplification reaction using the second primer set and an unmethylated cytosine conversion sample. On the other hand, in the case where the cytosine of the biological DNA that is the subject of hybridization is not converted into a base other than cytosine, the efficient production of the amplification product is not carried out. Accordingly, using a nucleic acid contained in the unmethylated cytosine conversion sample as a template, the amount of the amplification product obtained by a nucleic acid amplification using the second primer set is determined, whereby the accurate information about the amount of the converted nucleic acid contained in the unmethylated cytosine conversion sample can be obtained. The concrete second primer set in the case where human genome DNA is used as the biological DNA includes, for example, a primer set comprising a primer comprising a nucleotide sequence as shown in SEQ ID NO: 3 and a primer comprising a nucleotide sequence as shown in SEQ ID NO: 4, and the like.

Incidentally, it is preferable that the sequence of the 3'-terminal of the primer in the second primer set, particularly the 3'-end, is complementary to the base converted by the unmethylated cytosine conversion treatment. When the part that is not complementary to the template nucleic acid is present at the 3'-terminal of the primer, the efficiency of nucleic acid amplification reaction decreases. In other words, when the 3'-terminal of the primer in the second primer set is designed so as to be complementary to the base converted by the unmethylated cytosine conversion treatment, in the case where the nucleic acid in which cytosine of biological DNA is not converted into a base other than cytosine is used as a template, the efficiency of nucleic acid amplification reaction decreases. Therefore, according to the second primer set, there can be carried out more specific nucleic acid amplification reaction using the converted nucleic acid contained in the unmethylated cytosine conversion sample as a template. As a result, the amount of the amplification product obtained by the nucleic acid amplification using the second primer set having the primer designed as descried above can be determined to obtain more accurate information about the amount of a converted nucleic acid contained in the unmethylated cytosine conversion sample.

Incidentally, a tumor cell sometimes has a chromosomal abnormality in which the number of some chromosomes abnormally increases. Thus, when the first primer set and the second primer set are primer sets using the nucleic acid obtained by the unmethylated cytosine conversion treatment of each different chromosomal DNA as a template, whether or not the unmethylated cytosine conversion treatment is properly carried out cannot be accurately determined in some cases. Therefore, it is preferable that the nucleic acid obtained by the unmethylated cytosine conversion treatment of the same chromosome DNA of the above-described biological body is a template for both the first primer set and the second primer set. In other words, in the present invention, it is preferable that the nucleotide sequence not containing cytosine in the nucleotide sequence of biological DNA and the nucleotide sequence containing cytosine and not containing a CpG site in the biological DNA are present in the same chromosome of the biological body. As described above, when the first primer set and the second primer set are primer sets using as a template the nucleic acid derived from the same chromosome, even if the nucleic acid obtained by the unmethylated cytosine conversion treatment of DNA of a tumor cell which has an abnormality in the number of chromosomes is used, whether or not the unmethylated cytosine conversion treatment is properly carried out can be determined.

In addition, a tumor cell sometimes has other chromosomal abnormalities, for example, deletion, inversion, increase and decrease in the copy number of specific sequence, and the like. Thus, when the nucleic acid to be a template for one of the first primer set and the second primer set is derived from the region having a chromosomal abnormality, whether or not the unmethylated cytosine conversion treatment is properly carried out cannot be accurately determined in some cases. Therefore, it is preferable that, in the nucleic acid amplification method, the first primer set and the second primer set utilize the region close to each other in the nucleic acid contained in the unmethylated cytosine conversion sample as a template. Specifically, it is preferable that, in the nucleotide sequence of biological DNA that is subject to the unmethylated cytosine conversion treatment, the nucleotide sequence not containing cytosine complementary to at least one primer contained in the first primer set and the nucleotide sequence in which cytosine in a nucleotide sequence containing cytosine and not containing a CpG site complementary to at least one primer contained in the second primer set is converted into a base other than cytosine are contained in the nucleotide sequence of 300 bp or less. In other words, it is preferable that, in the nucleotide sequence of the nucleic acid contained in the unmethylated cytosine conversion sample, the nucleotide sequence with which at least one primer contained in the first primer set hybridizes and the nucleotide sequence with which at least one primer contained in the second primer set hybridizes are contained in the nucleotide sequence of 300 bp or less.

Furthermore, an overlapping region exists between a nucleic acid amplified by nucleic acid amplification using the first primer set and a nucleic acid amplified by nucleic acid amplification using the second primer set, and whereby the effects of chromosomal abnormality on the determination of whether or not the unmethylated cytosine conversion treatment is properly carried out can be further reduced. In other words, it is preferable that the same nucleotide sequence exists in both of a nucleotide sequence of the nucleic acid amplified by nucleic acid amplification using the unmethylated cytosine conversion sample and the first primer set and a nucleotide sequence of the nucleic acid amplified by nucleic acid amplification using the unmethylated cytosine conversion sample and the second primer set. More specifically, it is preferable that (1) at least one primer contained in the first primer set is a primer that hybridizes with the nucleic acid amplified by nucleic acid amplification using the second primer set, or (2) at least one primer contained in the second primer set is a primer that hybridizes with a nucleic acid comprising a nucleotide sequence in which cytosine in a nucleotide acid amplified by nucleic acid amplification using the first primer set is converted into a base other than cytosine.

In the kit of the present invention, each primer in the first primer set and each primer in the second primer set can be respectively provided in a separate container. The primer may be provided in the dry state and may be provided in a state dissolved in a solvent. The solvent for dissolving the primer includes nuclease-free purified water (for example, PCR grade water) and a buffer suitable for stably maintaining a nucleic acid. The buffer suitable for stably maintaining a nucleic acid includes, for example, TE buffer heat-treated to inactivate nuclease, microorganism and the like [composition: 10 mM Tris-HCl buffer (pH 8.0) and 1 mM EDTA], and the like.

The first primer set and the second primer set contained in the kit of the present invention can be suitably used for the determination of whether or not the unmethylated cytosine conversion treatment is properly carried out. The present invention also encompasses a method for determining whether or not the unmethylated cytosine conversion treatment is properly carried out by using the first primer set and the second primer set.

The method for determining whether or not the unmethylated cytosine conversion treatment is properly carried out according to the present invention (hereinafter also referred to as "the determination method of the present invention") is characterized by comprising the steps of:

(A) converting unmethylated cytosine of biological DNA contained in a sample into a base other than cytosine, to give an unmethylated cytosine conversion sample;

(B) carrying out nucleic acid amplification reactions of the following (i) and (ii):

(i) a nucleic acid amplification reaction using the unmethylated cytosine conversion sample obtained in the step (A) and the first primer set comprising plural primers that hybridize with a nucleic acid comprising a nucleotide sequence not containing cytosine in the nucleotide sequence of the biological DNA and (ii) a nucleic acid amplification reaction using the unmethylated cytosine conversion sample obtained in the step (A) and the second primer set comprising plural primers that hybridize with a nucleic acid comprising a nucleotide sequence in which cytosine in a nucleotide sequence containing cytosine and not containing a CpG site is converted into a base other than cytosine in the nucleotide sequence of the biological DNA;

(C) determining the amount of the amplification product obtained in the nucleic acid amplification reaction (i) and the amount of the amplification product obtained in the nucleic acid amplification reaction (ii) of the step (B);

(D) calculating the ratio of the nucleic acid in which the unmethylated cytosine of the biological DNA is converted into a base other than cytosine (converted nucleic acid) in total nucleic acids contained in the unmethylated cytosine conversion sample obtained in the step (A), based on the determination result obtained in the step (C); and (E) determining whether or not the step (A) is properly carried out, based on the calculation result obtained in the step (D).

The determination method of the present invention has one significant feature in that a nucleic acid amplification reaction using the unmethylated cytosine conversion sample and the first primer set is carried out in order to determine the amount of DNA in the unmethylated cytosine conversion sample, and also a nucleic acid amplification reaction using the unmethylated cytosine conversion sample and the second primer set is carried out in order to determine the amount of the converted nucleic acid in the unmethylated cytosine conversion sample.

FIG. 1 shows a flow chart showing one embodiment of the determination method of the present invention.

In the determination method of the present invention, first, unmethylated cytosine of biological DNA contained in a sample is converted into a base other than cytosine, to give an unmethylated cytosine conversion sample (Step S1). Step S1 corresponds to the step (A) described above.

A biological DNA-containing sample can be obtained by the known method. For example, a biological DNA-containing sample can be prepared by extracting DNA from a tissue or a cell of a biological body and dissolved into water or buffer. The extraction of DNA can be carried out by using, for example, the known method such as a phenol extraction method and a phenol-chloroform extraction method and also a commercially available DNA extraction kit. The water or buffer for dissolving DNA is preferably one that can stably maintain dissolved DNA. The water or buffer for dissolving DNA includes, for example, nuclease-free PCR-grade water, TE buffer [composition: 10 mM Tris-HCl buffer (pH 8.0) and 1 mM EDTA], and the like.

The conversion of unmethylated cytosine of biological DNA contained in a sample can be carried out by an unmethylated cytosine conversion treatment in which the above-described unmethylated cytosine conversion agent is brought into contact with the biological DNA. When bisulfite is used as the unmethylated cytosine conversion agent, methylated cytosine is not converted as described above, and unmethylated cytosine is converted into uracil.

In Step S1, in the case of an unmethylated cytosine conversion treatment using, for example, sodium hydrogen sulfite that is bisulfite, a sodium hydrogen sulfite solution is added to a biological DNA-containing sample, and the resulting mixture is incubated under the condition of appropriate temperature, whereby the unmethylated cytosine of biological DNA can be converted into uracil. The amount of bisulfite added to the biological DNA-containing sample is preferably the amount to be 3 M or more as the concentration of bisulfite in an unreacted mixture containing the bisulfite and the biological DNA. In the unmethylated cytosine conversion treatment, when a sodium hydrogen sulfite solution is added, for example, to a sample containing 2 μg of biological DNA so as to have a final concentration of 5 M, the reaction time of the sodium hydrogen sulfite solution with the biological DNA-containing sample can be set from 40 minutes to 16 hours, the reaction temperature can be set at from 50° to 80° C. Incidentally, the reaction conditions of the unmethylated cytosine conversion treatment are not limited to the reaction conditions described above and can be properly set.

Next, using the unmethylated cytosine conversion sample obtained in Step S1, a nucleic acid amplification reaction using the first primer set (Step S2) and a nucleic acid amplification reaction using the second primer set (Step S3) are carried out. Step S2 corresponds to the nucleic acid amplification reaction (i) of the step (B). Also, Step S3 corresponds to the nucleic acid amplification reaction (ii) of the step (B). The nucleic acid amplification reaction in Step S2 is for the confirmation of the amount of total nucleic acids, and the nucleic acid amplification reaction in Step S3 is for the confirmation of the amount of a converted nucleic acid.

The nucleic acid amplification reactions in Step S2 and Step S3 are carried out by the nucleic acid amplification reaction method described above, for example, the PCR method, the strand displacement reaction method, the LCR method, the transcription amplification method, or the like. Among these nucleic acid amplification methods, from the viewpoint of rapid and easy determination of an amplification product set forth below, a real-time PCR that is one of the PCR methods and a real-time LAMP that is one of the strand displacement reaction methods are preferable. When a nucleic acid is amplified by the PCR method or the LAMP method, the optical conditions (turbidity, absorbance, fluorescence intensity and the like) of the reaction solution are changed with progress of the nucleic acid amplification. Therefore, in the real-time PCR method or the real-time LAMP method, these optical conditions can be determined in real time to determine quantitatively the amount of the amplification product.

Subsequently, the amount of the amplification product obtained in the nucleic acid amplification reactions in Step S2 and Step S3 is determined (Step S4). Step S4 corresponds to the step (C).

When the real-time PCR method is used as the nucleic acid amplification methods in Step S2 and Step S3 described above, amplification product DNA is monitored in real time, and the DNA is quantified in an exponential amplification region. Therefore, the DNA can be accurately quantified based on amplification kinetics in the polymerase chain reaction. The real-time PCR method includes an intercalator method using an intercalator that emits fluorescence and a probe method using a probe (for example, TaqMan probe, a cycling probe, and the like) comprising a fluorescent dye-labeled oligonucleotide specific for a sequence of an amplification product. Among them, the intercalator method is preferable from the viewpoint of easy detection and quantification of the amplification product. In the intercalator method, an intercalator is a substance that binds to double-stranded DNA synthesized by a polymerase chain reaction and emits fluorescence upon irradiation with exciting light. In the intercalator method, the amount of the amplification product formed can be monitored by detecting fluorescence intensity based on the fluorescence of the intercalator that is bound to the amplification product obtained as double-stranded DNA. The intercalator includes, for example, SYBR (registered trademark) green manufactured by Molecular Probe Inc., and the like.

When a real-time LAMP method is used as the nucleic acid amplification methods in Step S2 and Step S3 described above, magnesium pyrophosphate formed as a byproduct with progress of nucleic acid amplification can be determined as an indicator of the amplification product. More specifically, magnesium pyrophosphate is insoluble in water, and thus the reaction solution becomes cloudy as magnesium pyrophosphate is increased. Accordingly, the amount of the amplification product can be quantitatively determined by measuring optically the turbidity (or absorbance) of the reaction solution in real time. The intercalator method described above can also be used in the real-time LAMP method.

Incidentally, in Step S4, the amount of the amplification product is calculated based on the calibration curve. The calibration curve can be prepared by the known method. For example, the calibration curve can be prepared from an amplification curve, the copy number of the standard DNA, the cycle number of reactions and the like, obtained by carrying out a nucleic acid amplification reaction using the standard DNA and each primer set and monitoring the amount of each amplification product in real time.

Then, the ratio of a converted nucleic acid in total nucleic acids contained in the unmethylated cytosine conversion sample is calculated (Step S5) based on the determination result of the amount of the amplification product in Step S4. Step S5 corresponds to the step (D).

For example, in accordance with according to the following equation (1):

[Amount of Amplification Product of Nucleic Acid Amplification Reaction (ii) Using Second Primer Set]/[Amount of Amplification Product of Nucleic Acid Amplification Reaction (i) Using First Primer Set]×100(%)     (1)

the ratio of a converted nucleic acid in total nucleic acids contained in the unmethylated cytosine conversion sample can be calculated.

Next, whether or not the unmethylated cytosine conversion treatment is properly carried out is determined based on the calculation result in Step S5 (Step S6). Step S6 corresponds to the step (E).

When the ratio of a converted nucleic acid in total nucleic acids contained in the unmethylated cytosine conversion sample is calculated by using the equation (1) described above, it can be determined that the closer to 100% the calculation result, the unmethylated cytosine conversion treatment is properly carried out. On the other hand, it can be determined that the closer to 0% the calculation result, the unmethylated cytosine conversion treatment is not properly carried out. Also, a threshold is set, and it can be determined that the unmethylated cytosine conversion treatment is properly carried out when the calculation result is higher than the threshold, and can be determined that the unmethylated cytosine conversion treatment is not properly carried out when the calculation result is lower than the threshold. Here, the threshold can be obtained from the ratio of a converted nucleic acid in total nucleic acids contained in the unmethylated cytosine conversion sample and the accumulation of data on the analysis result of methylated DNA using the unmethylated cytosine conversion sample. The threshold may vary depending on the data accumulation amount, the type of the nucleic acid amplification reaction, the type of each primer set used, and the reaction conditions of the unmethylated cytosine conversion treatment. For example, the threshold can be set at 5 to 25% and preferably at 10 to 20%.

The determination method of the present invention can be easily carried out by using the kit of the present invention.

According to the kit of the present invention and the determination method of the present invention, whether or not the unmethylated cytosine conversion treatment carried out in an analysis of methylated DNA is properly carried out can be determined. Therefore, by using the kit and determination method of the present invention, the analysis of methylated DNA can be accurately carried out. Accordingly, the present invention also comprises a method for analyzing methylated DNA.

The method for analyzing methylated DNA of the present invention comprises:
(A) converting unmethylated cytosine of biological DNA contained in a sample into a base other than cytosine, to give an unmethylated cytosine conversion sample;
(B) carrying out nucleic acid amplification reactions of the following (i) and (ii):
 (i) a nucleic acid amplification reaction using the unmethylated cytosine conversion sample obtained in the step (A) and the first primer set comprising plural primers that hybridize with a nucleic acid comprising a nucleotide sequence not containing cytosine in the nucleotide sequence of the biological DNA and
 (ii) a nucleic acid amplification reaction using the unmethylated cytosine conversion sample obtained in the step (A) and the second primer set comprising plural primers that hybridize with a nucleic acid comprising a nucleotide sequence in which cytosine in a nucleotide sequence containing cytosine and not containing a CpG site is converted into a base other than cytosine in the nucleotide sequence of the biological DNA;
(C) determining the amount of the amplification product obtained in the nucleic acid amplification reaction (i) and the amount of the amplification product obtained in the nucleic acid amplification reaction (ii) of the step (B);
(D) calculating the ratio of the nucleic acid in which the unmethylated cytosine of the biological DNA is converted into a base other than cytosine in total nucleic acids contained in the unmethylated cytosine conversion sample obtained in the step (A), based on the determination result obtained in the step (C);
(E) determining whether or not the step (A) is properly carried out, based on the calculation result obtained in the step (D), and
(F) analyzing methylated DNA using the unmethylated cytosine conversion sample obtained in the step (A), when the step (A) is determined as properly carried out in the step (E).

The method for analyzing methylated DNA of the present invention has one significant feature in that, prior to the analysis of methylated DNA, whether or not the unmethylated cytosine conversion treatment is properly carried out is determined, and when the unmethylated cytosine conversion treatment is properly carried out, the analysis of methylated DNA is carried out. Therefore, since in the method for analyzing a methylated DNA of the present invention, the unmethylated cytosine conversion sample in which the unmethylated cytosine conversion treatment is properly carried out in order to analyze methylation is used, the method exhibits an excellent effect that methylated DNA can be accurately and efficiently analyzed.

Figure 2:
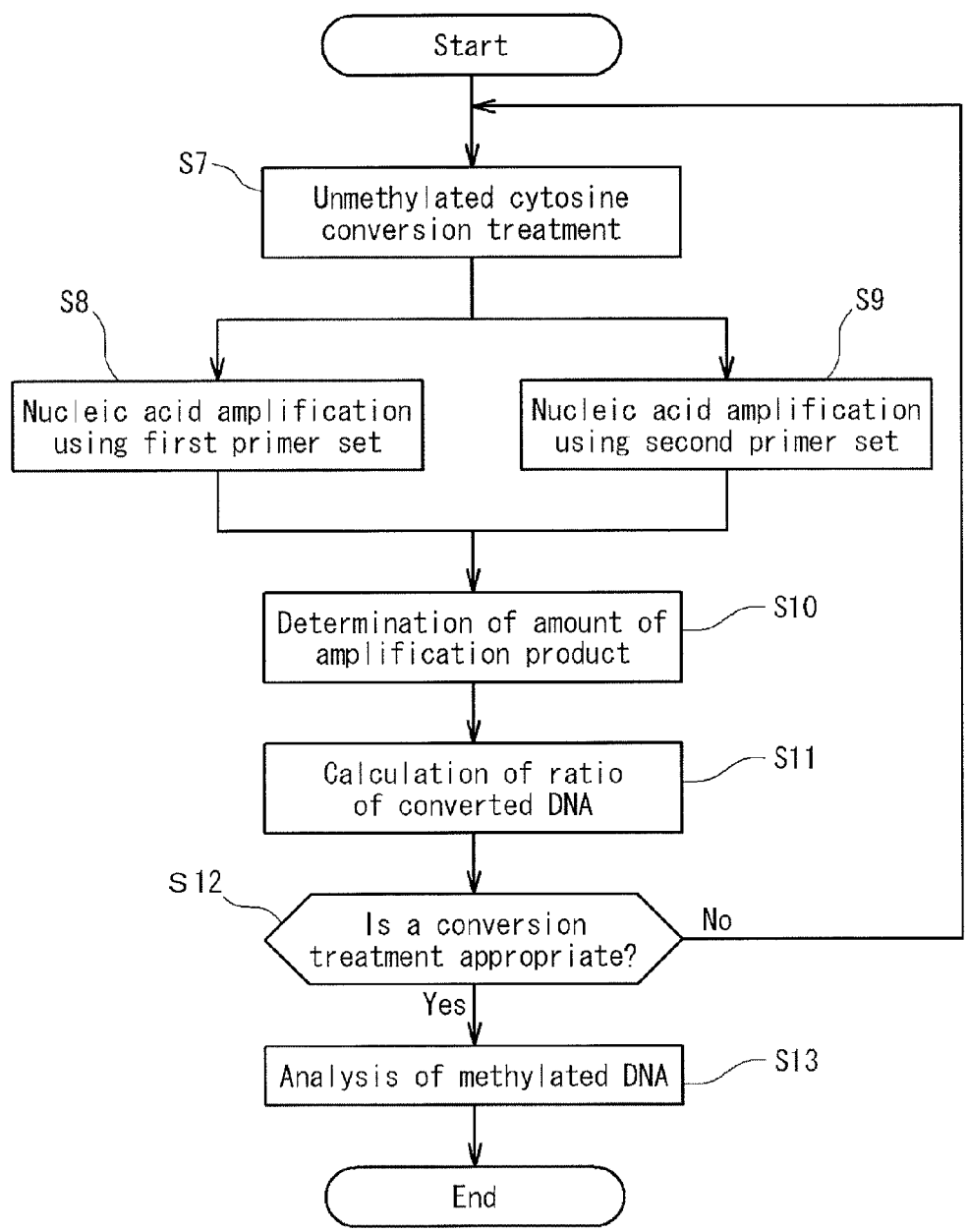
FIG. 2 is a flow chart showing one embodiment of the analysis method of the present invention.

FIG. 2 shows a flow chart showing one embodiment of the analysis method of the present invention.

The steps (A) to (E) are the same as the operations of the determination methods of the present invention. In addition, Steps S7 to S12 in FIG. 2 are the same as the operations of Steps S1 to S6 in FIG. 1.

In the method for analyzing methylated DNA of the present invention, when the unmethylated cytosine conversion treatment is determined to be properly carried out in Step S12 [step (E)], the analysis of methylated DNA is carried out by using the unmethylated cytosine conversion sample (Step S13). Incidentally, when the unmethylated cytosine conversion treatment is not properly carried out, the process is returned to Step S7 [step (A)], the operation of obtaining the unmethylated cytosine conversion sample may be carried out again.

The analysis of methylated DNA is carried out, for example, by the methylation specific PCR method, a method for analyzing nucleotide sequence of the nucleic acid in the unmethylated cytosine conversion sample, and an analysis method using DNA chips in which DNA of a disease-related gene, DNA of a transcription factor, DNA of an expression regulation factor, DNA of a promoter region, and the like are immobilized. The DNA chips are preferably tiling arrays wherein nucleotide sequences taken out at regular intervals from decoded genomic data in gene expression information are fixed as detection probes in the form of tiles.

In the method for analyzing methylated DNA of the present invention, the analysis of methylated DNA can be carried out by using a proper unmethylated cytosine conversion sample. Therefore, the method allows, for example, high throughput analysis or high throughput screening of a gene of which in vivo kinetic changes due to methylation of a CpG site, the onset of disease, a factor indicating the progression of disease status, a factor targeted by a drug, or the like.

Hereinafter, the present invention will be described in detail with reference to Examples, but the present invention is not limited to such Examples.

EXAMPLES

Example 1

Based on the nucleotide sequence of human genomic DNA, as a primer set using a nucleotide sequence comprising a part of the human genomic DNA (SEQ ID NO: 7) as a target sequence, a primer set comprising two types of primers that hybridized with a nucleic acid comprising a nucleotide sequence not containing cytosine was designed to synthesize each primer.

As a result, a primer set comprising a forward primer comprising a nucleotide sequence as shown in SEQ ID NO: 1 and a reverse primer comprising a nucleotide sequence as shown in SEQ ID NO: 2 was obtained. The resulting primer set was defined as a primer set 1 for confirmation of the amount of total nucleic acids contained in a human-derived sample (hereinafter, referred to as "primer set 1 for checking an amount of a nucleic acid"). A forward primer and a reverse primer in the resulting primer set 1 for checking an amount of a nucleic acid were each dissolved in separate nuclease-free purified water so as to have a final concentration of 10 μM, to give an aqueous forward primer solution and aqueous reverse primer solution of the primer set 1 for checking an amount of a nucleic acid.

In addition, based on the nucleotide sequence of human genomic DNA, among nucleotide sequences containing cytosine and not containing a CpG site, a primer set comprising two types of primers that hybridized with a nucleic acid comprising a nucleotide sequence in which cytosine was converted into a base other than cytosine (uracil) was designed to synthesize each primer.

As a result, a primer set comprising a forward primer comprising a nucleotide sequence as shown in SEQ ID NO: 5 and a reverse primer comprising a nucleotide sequence as shown in SEQ ID NO: 6 was obtained. The resulting primer set was used as a primer set for confirmation of the amount of a converted nucleic acid contained in total nucleic acids (hereinafter, referred to as "primer set 1 for checking a conversion treatment"). A forward primer and a reverse primer in the resulting primer set 1 for checking a conversion treatment were each dissolved in separate nuclease-free purified water so as to have a final concentration of 10 μM, to give an aqueous forward primer solution and aqueous reverse primer solution of the primer set for checking a conversion treatment.

The aqueous forward primer solution and aqueous reverse primer solution of the primer set 1 for checking an amount of a nucleic acid were each enclosed in a separate nuclease-free container. In addition, the aqueous forward primer solution and aqueous reverse primer solution of the primer set 1 for checking a conversion treatment were each enclosed in a separate nuclease-free container. The combination of the primer set 1 for checking an amount of a nucleic acid and the primer set 1 for checking a conversion treatment was defined as a kit for determination of unmethylated cytosine conversion treatment of Experimental Example 1.

Example 1

Preparation of Analytical Sample

To two microgram of genomic DNA derived from a normal human mammary tissue (manufactured by BioChain Institute, Inc.), 300 μL of 0.3M aqueous sodium hydroxide solution was added and thereafter the resulting mixture was incubated at 37° C. for 10 minutes. Subsequently, a product after incubation was subjected to bisulfite treatment by adding 300 μL of 10 M sodium hydrogen sulfite solution thereto and incubating the resulting mixture at 80° C. for 40 minutes. Thereafter, a nucleic acid contained in the product obtained by the bisulfite treatment was purified with a nucleic acid purification kit (manufactured by QIAGEN under the trade name of Qiaquick PCR purification kit,). Sodium hydroxide was added to the resulting nucleic acid so as to have a final concentration of 0.3 M, and the resulting mixture was incubated at room temperature for 5 minutes. The resulting product was purified through a spin column for nucleic acid purification (manufactured by GE Healthcare under the trade name of MicroSpin S-300 HR Columns), to give analysis sample 1.

The same operations were carried out by using genomic DNA derived from a different type of genomic DNA derived from a normal human mammary tissue (manufactured by BioChain Institute, Inc.) from the genomic DNA derived from a normal human mammary tissue used in the preparation method of analysis sample 1 described above, to give analysis sample 2.

(Determination of Amount of Amplification Product of Quantitative PCR for Confirmation of Amount of Nucleic Acids)

Next, in order to determine whether the bisulfite treatment was properly carried out in each of analysis samples 1 and 2, the following quantitative PCR was carried out by using the kit for determination of unmethylated cytosine conversion treatment of Experimental Example 1.

Twelve point five microliters of a reagent for nucleic acid amplification (manufactured by Roche Diagnostics K.K. under the trade name of FastStart SYBR Green Master Mix), 1 μL of an aqueous forward primer solution (10 μM) of the primer set 1 for checking an amount of a nucleic acid and 1 μL of an aqueous reverse primer solution (10 μM) of an aqueous forward primer solution of the primer set 1 for checking an amount of a nucleic acid contained in the kit for determination of unmethylated cytosine conversion treatment of Experimental Example 1 and 9.5 μL of water were added to 1 μL of analytical sample 1 or analytical sample 2, thereby preparing a reaction solution for PCR. The reaction solution for PCR was used to carry out quantitative PCR. Incidentally, the reaction conditions in the quantitative PCR were conditions for carrying out the reaction of incubation at 95° C. for 10 minutes followed by 40 cycles of the reaction, each cycle being 95° C. for 30 seconds, 62° C. for 30 seconds and 72° C. for 30 seconds, and subsequently carrying out the reaction being 95° C. for 60 seconds, 62° C. for 30 seconds and 95° C. for 30 seconds.

The amount of an amplification product by the quantitative PCR using the primer set 1 for checking an amount of a nucleic acid was calculated based on the calibration curve prepared by the quantitative PCR using the primer set 1 for checking an amount of a nucleic acid and the standard DNA comprising a nucleotide sequence as shown in SEQ ID NO: 9.

(Determination of Amount of Amplification Product of Quantitative PCR for Confirmation of Amount of Converted Nucleic Acid)

Next, quantitative PCR was carried out in the same manner as in the above except that the primer set 1 for checking a conversion treatment contained in the kit for determination of unmethylated cytosine conversion treatment of Experimental Example 1 was used in place of the primer set 1 for checking an amount of a nucleic acid.

The amount of an amplification product by the quantitative PCR using the primer set 1 for checking a conversion treatment was calculated based on the calibration curve prepared by the quantitative PCR using the primer set for checking a conversion treatment and the standard DNA comprising a nucleotide sequence as shown in SEQ ID NO: 10.

(Calculation of Ratio of Amount of Converted Nucleic Acid Contained in Total Nucleic Acids)

Figure 3:
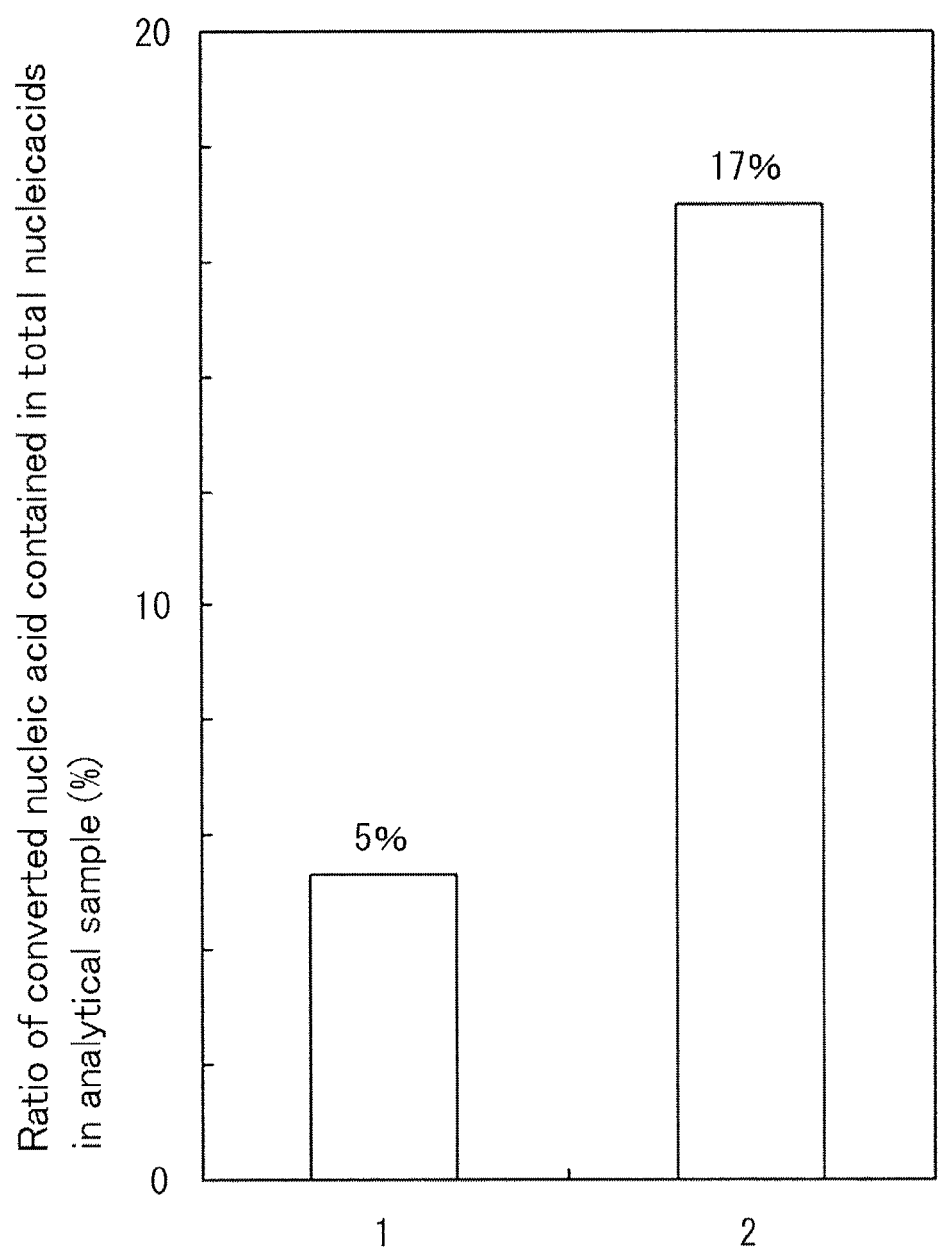
FIG. 3 is a graph showing the result of calculating the ratio of converted nucleic acid contained in total nucleic acids in an analysis sample in Example 1.

From the amount of an amplification product of quantitative PCR for confirmation of the amount of total nucleic acids and the amount of an amplification product of quantitative PCR for confirmation of the amount of converted nucleic acid, based on the equation (2):

[Amount of Amplification Product of Quantitative PCR for Confirmation of Amount of Converted Nucleic Acid]/[Amount of Amplification Product of Quantitative PCR for Confirmation of Amount of Total nucleic acids]×100(%)    (2)

the ratio of a converted nucleic acid contained in total nucleic acids in the analysis sample was calculated as "the ratio of the amount of a converted nucleic acid to the amount of total nucleic acids contained in analysis sample 1 or analysis sample 2". The results are shown in FIG. 3. In FIG. 3, bar 1 shows the result when analysis sample 1 and the kit for determination of unmethylated cytosine conversion treatment of Experimental Example 1 are used. Bar 2 shows the result when analysis sample 2 and the kit for determination of unmethylated cytosine conversion treatment of Experimental Example 1 are used.

From the results shown in FIG. 3, it was revealed that, by using the kit for determination of unmethylated cytosine conversion treatment of Experimental Example 1, the ratio of a converted nucleic acid contained in total nucleic acids in the sample after the bisulfite treatment can be determined for tissue-derived DNA. In addition, from these results, it is suggested that whether or not an unmethylated cytosine conversion treatment of DNA such as bisulfite treatment is properly carried out can be determined based on the ratio of a converted nucleic contained in total nucleic acids in the analysis sample.

Experimental Example 2

Based on a nucleotide sequence as shown in SEQ ID NO: 7, a primer set comprising two types of primers was designed to synthesize each primer, wherein the primers were primers that hybridized with a nucleic acid comprising a nucleotide sequence in which cytosine was substituted by a base other than cytosine (uracil) among nucleotide sequences not containing a CpG site and containing cytosine.

As a result, a primer set comprising a forward primer comprising a nucleotide sequence as shown in SEQ ID NO: 3 and a reverse primer comprising a nucleotide sequence as shown in SEQ ID NO: 4 was obtained. The resulting primer set was used as a primer set for confirmation of whether or not an unmethylated cytosine conversion treatment is properly carried out by confirming the amount of a converted nucleic acid contained in total nucleic acids (hereinafter, referred to as "primer set 2 for checking a conversion treatment").

A forward primer and reverse primer in the primer set 2 for checking a conversion treatment were each dissolved in separate nuclease-free purified water so as to have a final concentration of 10 µM, to give an aqueous forward primer solution and aqueous reverse primer solution of the primer set 2 for checking a conversion treatment.

The aqueous forward primer solution and aqueous reverse primer solution of the primer set 1 for checking an amount of a nucleic acid were each enclosed in a separate nuclease-free container. In addition, the aqueous forward primer solution and aqueous reverse primer solution of the primer set 2 for checking a conversion treatment were each enclosed in a separate nuclease-free container. The combination of the primer set 1 for checking an amount of a nucleic acid and the primer set 2 for checking a conversion treatment was defined as a kit for determination of unmethylated cytosine conversion treatment of Experimental Example 2.

Figure 4:
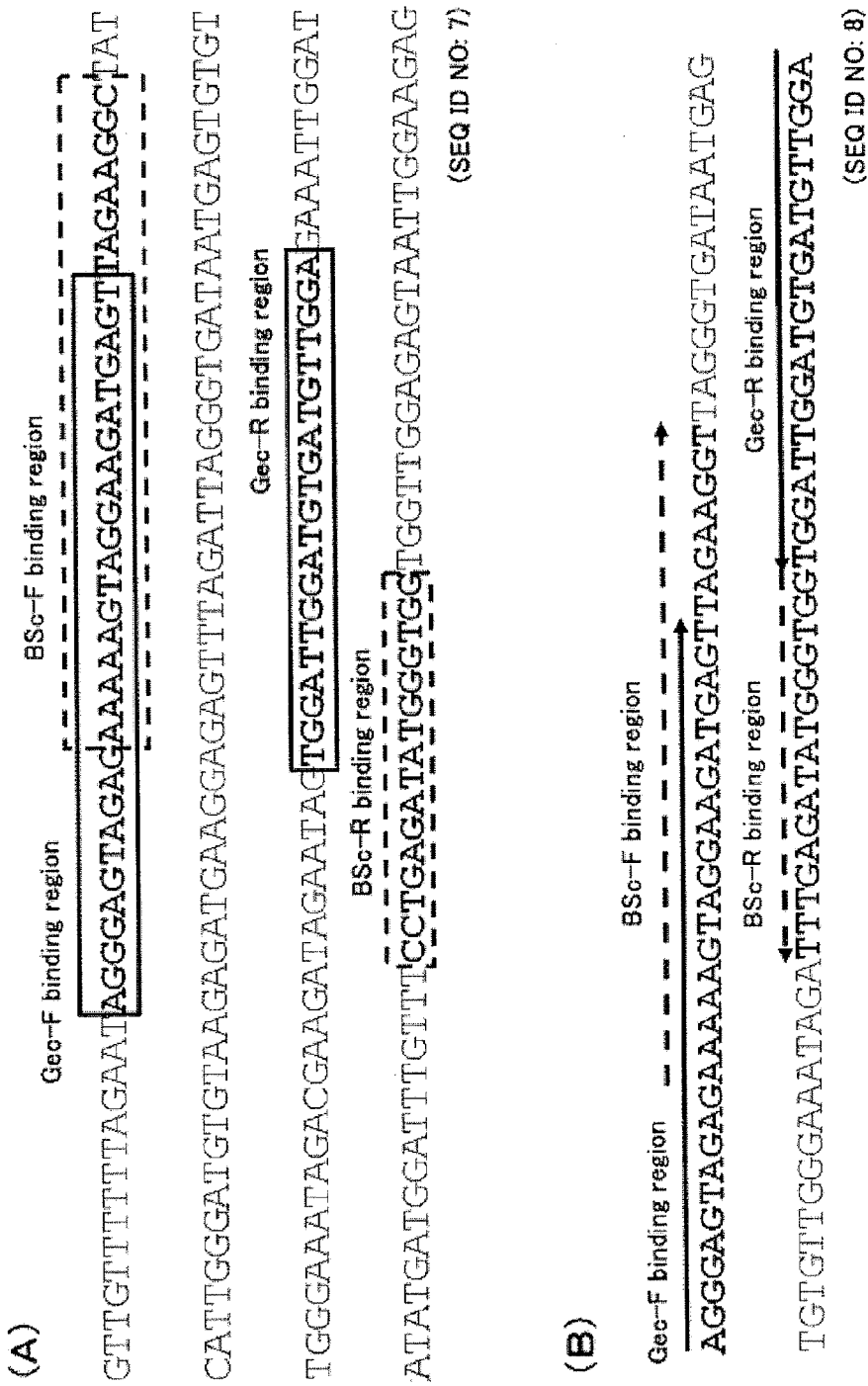
FIG. 4 (A) is a schematic diagram showing a binding region of each primer in primer set 1 for checking an amount of a nucleic acid and primer set 2 for checking a conversion treatment in a nucleotide sequence as shown in SEQ ID NO: 7.

Binding regions of each primer of the primer set 1 for checking an amount of a nucleic acid and the primer set 2 for checking a conversion treatment on the nucleotide sequence as shown in SEQ ID NO: 7 are shown in FIG. 4 (A). In FIG. 4 (A), Gec-F binding region shows a binding region of a forward primer of the primer set 1 for checking an amount of a nucleic acid. Gec-R binding region shows a binding region of a reverse primer of the primer set 1 for checking an amount of a nucleic acid. BSc-F binding region shows a binding region of a forward primer of the primer set 2 for checking a conversion treatment. BSc-R binding region shows a binding region of a reverse primer of the primer set 2 for checking a conversion treatment. Incidentally, a binding region of each primer of the primer set 2 for checking a conversion treatment shows as a region where each primer hybridizes with a nucleic acid in which cytosine in the target sequence is converted into uracil.

Preparation Example 1

Using a DNA extraction kit (manufactured by QIAGEN under the trade name of QIAmp Blood Maxi Kit), genomic DNA was extracted from breast cancer cell line MCF7. To two micrograms of the resulting genomic DNA, 300 µL of 0.3 M aqueous sodium hydroxide solution was added, and the resulting mixture was incubated at 37° C. for 10 minutes. Subsequently, a product after incubation was subjected to bisulfite treatment by adding 300 µL of 10 M sodium hydrogen sulfite solution thereto and incubating the resulting mixture at 80° C. for 40 minutes. A nucleic acid contained in the resulting product was purified with a nucleic acid purification kit (manufactured by QIAGEN under the trade name of Qiaquick PCR purification kit). Sodium hydroxide was added to the resulting nucleic acid so as to have a final concentration of 0.3 M, and the resulting mixture was incubated at room temperature for 5 minutes. The resulting product was purified with a spin column for nucleic acid purification (manufactured by GE Healthcare under the trade name of MicroSpin S-300 HR Columns), to give an analysis sample of Preparation Example 1.

Preparation Example 2

To two micrograms of the genomic DNA extracted from breast cancer cell line MCF7 by carrying out the same operations as those in Preparation Example 1, 56 µL of 0.2 M aqueous sodium hydroxide solution was added and the resulting mixture was incubated at 37° C. for 10 minutes. Subsequently, a product after incubation was subjected to bisulfite treatment by adding 30 µL of 0.11 g/L aqueous hydroquinone solution and 520 µL of 3 M sodium hydrogen sulfite solution thereto and incubating the resulting mixture at 50° C. for 16 hours. A nucleic acid contained in the resulting product was purified with a nucleic acid purification kit (manufactured by QIAGEN under the trade name of Qiaquick PCR purification kit). Sodium hydroxide was added to the resulting nucleic acid so as to have a final concentration of 0.3 M, and the resulting mixture was incubated at room temperature for 5 minutes. The resulting product was purified with a spin column for nucleic acid purification (manufactured by GE Healthcare under the trade name of MicroSpin S-300 HR Columns), to give an analysis sample of Preparation Example 2.

Test Example 1

In order to confirm whether or not bisulfite treatments of the analysis sample of Preparation Example 1 and the analysis sample of Preparation Example 2 were properly carried out, quantitative PCR for confirmation of the amount of nucleic acids and quantitative PCR for confirmation of the amount of a converted nucleic acid were carried out by using the kit for determination of unmethylated cytosine conversion treatment of Experimental Example 1 and the kit for determination of unmethylated cytosine conversion treatment of Experimental Example 2.
(Determination of Amount of Amplification Product of Quantitative PCR for Confirmation of Amount of Nucleic Acids)

The quantitative PCR for determination of the amount of nucleic acids was carried out in the same manner as in Experimental Example 1 except that the analysis sample of Preparation Example 1 and the analysis sample of Preparation Example 2 were used in place of analysis sample 1 and analysis sample 2 in Experimental Example 1, respectively.

The amount of an amplification product by the quantitative PCR using the primer set 1 for checking an amount of a nucleic acid was calculated based on the calibration curve prepared by the quantitative PCR using the primer set 1 for checking an amount of a nucleic acid and the standard DNA comprising a nucleotide sequence as shown in SEQ ID NO: 8. Incidentally, a binding region of each primer of the primer set 1 for checking an amount of a nucleic acid on the standard DNA comprising the nucleotide sequence as shown in SEQ ID NO: 8 is shown in FIG. 4 (B). In FIG. 4 (B), Gec-F binding region shows a binding region of a forward primer of the primer set 1 for checking an amount of a nucleic acid. Gec-R binding region shows a binding region of a reverse primer of the primer set 1 for checking an amount of a nucleic acid.
(Determination of Amount of Amplification Product of Quantitative PCR for Confirmation of Amount of Converted Nucleic Acid)

The quantitative PCR for confirmation of the amount of a converted nucleic acid was carried out in the same manner as in Example 1 except that the analysis sample of Preparation Example 1 or the analysis sample of Preparation Example 2 was used in place of the analysis sample 1 or the analysis sample 2 in Example 1.

The amount of an amplification product by the quantitative PCR using the primer set 2 for checking a conversion treatment was calculated based on the calibration curve prepared by the quantitative PCR using the primer set 2 for checking a conversion treatment 2 and the standard DNA comprising the nucleotide sequence as shown in SEQ ID NO: 8. Incidentally, a binding region of each primer of the primer set 2 for checking a conversion treatment on the standard DNA comprising the nucleotide sequence as shown in SEQ ID NO: 8 is shown in FIG. 4 (B). In FIG. 4 (B), BSc-F binding region shows a binding region of a forward primer of the primer set 2 for checking a conversion treatment. BSc-R binding region shows a binding region of a reverse primer of the primer set 2 for checking a conversion treatment.

(Calculation of Ratio of Amount of Converted Nucleic Acid in Amount of Total Nucleic Acids)

The ratio of a converted nucleic acid contained in total nucleic acids in the analysis sample was calculated from the amount of an amplification product of the quantitative PCR for confirmation of the amount of nucleic acids and the amount of an amplification product of the quantitative PCR for confirmation of the amount of a converted nucleic acid, based on the equation (2) described above. The results are shown in FIG. 5.

Figure 5:
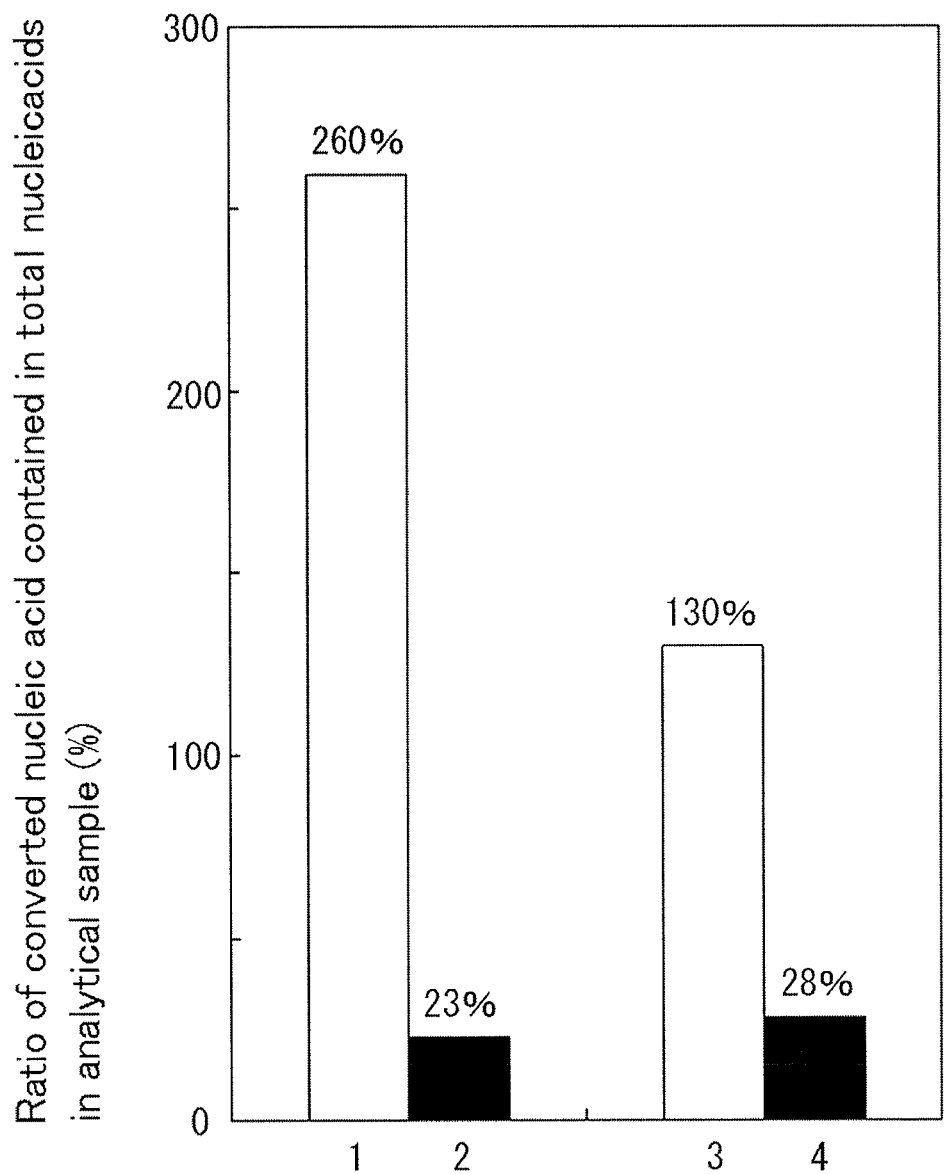
FIG. 5 is a graph showing the result of calculating the ratio of converted nucleic acid contained in total nucleic acids in an analysis sample in Test Example 1.

In FIG. 5, bar 1 shows the result of a case where the analysis sample of Preparation Example 1 and the kit for determination of unmethylated cytosine conversion treatment of Experimental Example 1 were used. Bar 2 shows the result of a case where the analysis sample of Preparation Example 1 and the kit for determination of unmethylated cytosine conversion treatment of Experimental Example 2 were used. Bar 3 shows the result of a case where the analysis sample of Preparation Example 2 and the kit for determination of unmethylated cytosine conversion treatment of Experimental Example 1 were used. Bar 4 shows the result of a case where the analysis sample of Preparation Example 2 and the kit for determination of unmethylated cytosine conversion treatment of Experimental Example 2 were used.

A binding region of a primer contained in the primer set 1 for checking a conversion treatment of the kit for determination of unmethylated cytosine conversion treatment of Experimental Example 1 is present in a different type of chromosome from a chromosome in which a region as shown in SEQ ID NO: 7 is present. Thus, when any copy numbers of the regions amplified by primers contained in the primer set 1 for checking an amount of a nucleic acid and the primer set 1 for checking a conversion treatment of the kit for determination of unmethylated cytosine conversion treatment of Experimental Example 1 varies due to chromosomal abnormalities, there are differences in a variation in the absolute amount between the amplification product by a nucleic acid amplification reaction using the primer set 1 for checking an amount of a nucleic acid and the amplification product by a nucleic acid amplification reaction using the primer set 2 for checking a conversion treatment. Therefore, it is considered that the abnormal value of the ratio of a converted nucleic acid contained in total nucleic acids when using the kit for determination of unmethylated cytosine conversion treatment of Experimental Example 1 is caused by chromosomal abnormalities in a tumor cell.

On the other hand, binding regions of all primers contained in the primer set 1 for checking conversion treatment and the primer set 2 for checking a conversion treatment of the kit for determination of unmethylated cytosine conversion treatment of Experimental Example 2 are present in the region comprising a highly limited target sequence as show in SEQ ID NO: 7 (224 bp) in human genomic DNA (see FIG. 4). In other words, in the kit for determination of unmethylated cytosine conversion treatment of Experimental Example 2, a nucleotide sequence of a part with which the primer contained in the primer set 1 for checking an amount of a nucleic acid hybridizes and a nucleotide sequence of a part with which the primer contained in the primer set 2 for checking a conversion treatment hybridizes are contained in the 224 bp nucleotide sequence.

Therefore, assuming that, in the region comprising the target sequence described above, even when chromosomal abnormalities are caused, the chromosomal abnormalities affect in the same manner on both of the nucleic acid amplification reaction using the primer set 1 for checking an amount of a nucleic acid and the nucleic acid amplification reaction using the primer set 2 for checking a conversion treatment. In other words, even if the absolute amount of each of the amplification product by the nucleic acid amplification reaction using the primer set 1 for checking an amount of a nucleic acid and the amplification product by the nucleic acid amplification reaction using the primer set 2 for checking a conversion treatment varies, the ratio of a converted nucleic acid contained in total nucleic acids does not vary.

As described above, it was revealed that according to the kit for determination of unmethylated cytosine conversion treatment of Experimental Example 2, whether or not an unmethylated cytosine conversion treatment of tumor cell genomic DNA in which chromosomal abnormalities were frequently caused was properly carried out could be accurately determined.

Preparation Example 3

To two micrograms of the genomic DNA extracted from breast cancer cell line MCF7 by carrying out the same operations as those in Preparation Example 1 300 µL of serum from a healthy subject was added, thereby preparing a serum-containing sample. DNA contained in the prepared serum-containing sample was purified with a nucleic acid purification kit (manufactured by QIAGEN under the trade name of Qiaquick PCR purification kit). To the purified DNA, 300 µL of 0.3 M aqueous sodium hydroxide solution was added, and the resulting mixture was incubated at 37° C. for 10 minutes. Subsequently, a product after incubation was subjected to bisulfite treatment by adding 300 µL of 10 M sodium hydrogen sulfite solution thereto and incubating the resulting mixture at 80° C. for 40 minutes. A nucleic acid contained in the resulting product was purified with a nucleic acid purification kit (manufactured by QIAGEN under the trade name of Qiaquick PCR purification kit). Sodium hydroxide was added to the resulting nucleic acid so as to have a final concentration of 0.3 M, and the resulting mixture was incubated at room temperature for 5 minutes. The resulting product was purified with a spin column for nucleic acid purification (manufactured by GE Healthcare under the trade name of MicroSpin S-300 HR Columns), to give an analysis sample of Preparation Example 3.

Preparation Example 4

To two micrograms of the genomic DNA extracted from breast cancer cell line MCF7 by carrying out the same operations as those in Preparation Example 1, 300 µL of serum from a healthy subject was added, thereby preparing a serum-containing sample. DNA contained in the prepared serum-containing sample was purified with a nucleic acid purification kit (manufactured by QIAGEN under the trade name of Qiaquick PCR purification kit). To the purified DNA, 300 μL of 0.3 M aqueous sodium hydroxide solution was added and the resulting mixture was incubated at 37° C. for 10 minutes. Subsequently, a product after incubation was subjected to bisulfite treatment by adding 30 mL of 0.11 g/L aqueous hydroquinone solution and 520 μL of 3 M sodium hydrogen sulfite solution thereto and incubating the resulting mixture at 50° C. for 16 hours. A nucleic acid contained in the resulting product was purified with a nucleic acid purification kit (manufactured by QIAGEN under the trade name of Qiaquick PCR purification kit). Sodium hydroxide was added to the resulting nucleic acid so as to have a final concentration of 0.3 M, and the resulting mixture was incubated at room temperature for 5 minutes. The resulting product was purified with a spin column for nucleic acid purification (manufactured by GE Healthcare under the trade name of MicroSpin S-300 HR Columns), to give an analysis sample of Preparation Example 4.

Preparation Example 5

Three hundred microliters of serum from a healthy subject, 300 μL of 18 M guanidine-HCl and 20 μL of 20 mg/mL Proteinase K (manufactured by Sigma) were added to 2 μg of the genomic DNA extracted from breast cancer cell line MCF7 by carrying out the same operations as those in Preparation Example 1, and the resulting mixture was incubated at 50° C. for 60 minutes. Subsequently, 20 μL of 10 M aqueous sodium hydroxide solution was added to a product after incubation, and the resulting mixture was incubated at 37° C. for 10 minutes. Thereafter, a product after incubation was subjected to bisulfite treatment by adding 640 μL of 10 M sodium hydrogen sulfite solution thereto and incubating the resulting mixture at 80° C. for 40 hours. A nucleic acid contained in the resulting product was purified with a nucleic acid purification kit (manufactured by QIAGEN under the trade name of Qiaquick PCR purification kit,). Sodium hydroxide was added to the resulting nucleic acid so as to have a final concentration of 0.3 M, and the resulting mixture was incubated at room temperature for 5 minutes. The resulting product was purified with a spin column for nucleic acid purification (manufactured by GE Healthcare under the trade name of MicroSpin S-300 HR Columns), to give an analysis sample of Preparation Example 5.

Example 2

Figure 6:
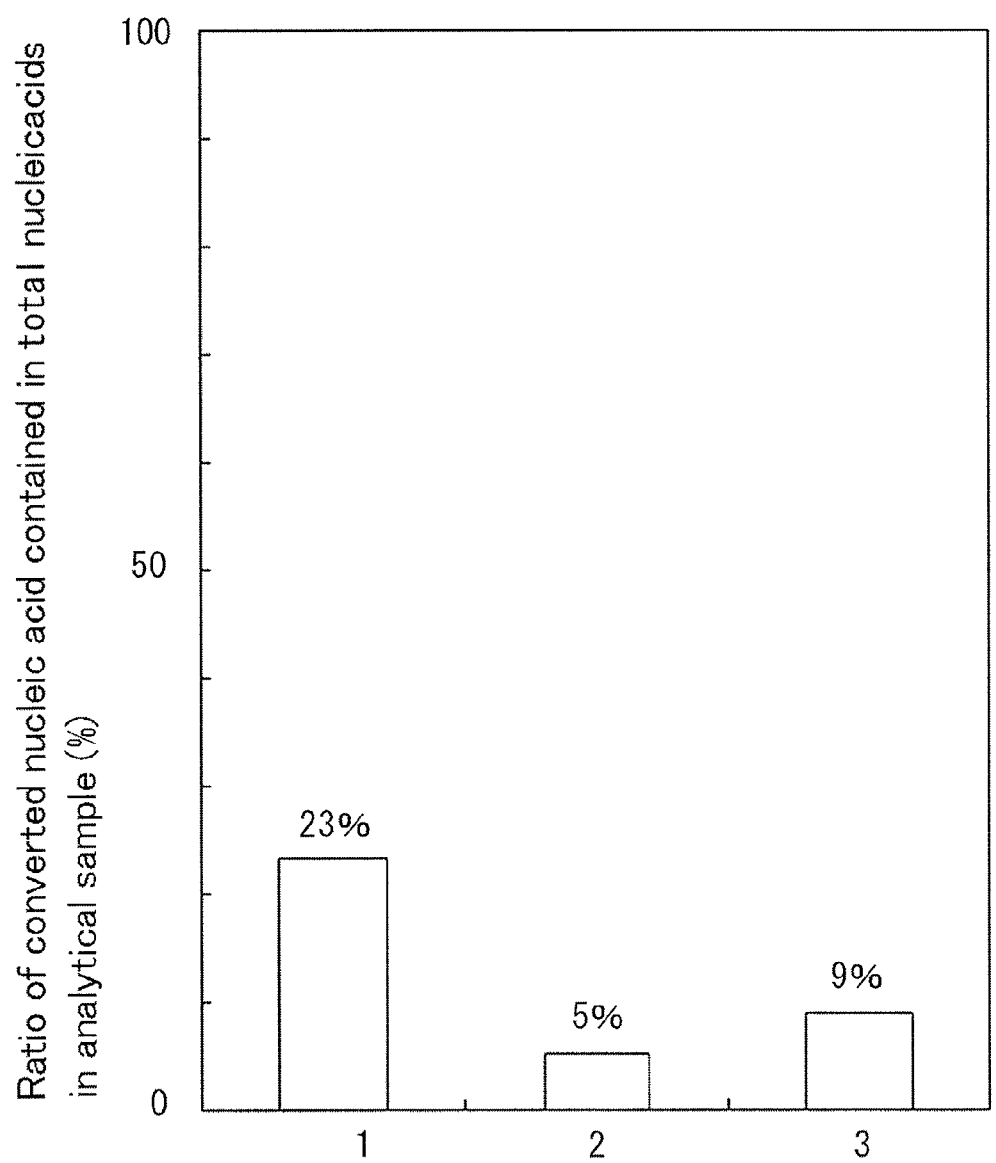
FIG. 6 is a graph showing the result of calculating the ratio of converted nucleic acid contained in total nucleic acids in an analysis sample in Example 2.

The ratio of a converted nucleic acid contained in total nucleic acids in the analysis sample was calculated by carrying out the same operations as those in Example 1 with the kit for determination of unmethylated cytosine conversion treatment of Experimental Example 2 except that any one of the analytical samples of Preparation Examples 3 to 5 was used in place of analytical sample 1 or analytical sample 2 in Example 1. The results are shown in FIG. 6. In FIG. 6, bar 1 shows the result of a case where the analysis sample of Preparation Example 3 was used. Bar 2 shows the result of a case where the analysis sample of Preparation Example 4 was used. Bar 3 shows the result of a case where the analysis sample of Preparation Example 5 was used.

From the results shown in FIG. 6, it was revealed that, by using the kit for determination of unmethylated cytosine conversion treatment of Experimental Example 2, for breast cancer cell line-derived DNA in which chromosomal abnormalities were frequently caused, the ratio of a converted nucleic acid contained in total nucleic acids in the sample after bisulfite treatment can be obtained. In addition, it was revealed that, according to the kit for determination of unmethylated cytosine conversion treatment of Experimental Example 2, the ratio of a converted nucleic acid contained in total nucleic acids in the sample after bisulfite treatment can be obtained, regardless of the method of bisulfite treatment. From these results, it is suggested that, even in the case of various unmethylated cytosine conversion treatments, whether or not the unmethylated cytosine conversion treatment is properly carried out can be determined based on the ratio of a converted nucleic acid contained in total nucleic acids in the analytical sample.

Preparation Examples 6 to 8

Using 3 types of genomic DNA 1 to 3 of human breast cancer tissue obtained from different patients (each manufactured by BioChain Institute, Inc.), analytical samples of Preparation Examples 6 to 8 were obtained as follows.

To two micrograms of the human breast cancer tissue genomic DNA described above, 300 μL of 0.3 M aqueous sodium hydroxide solution was added and the resulting mixture was incubated at 37° C. for 10 minutes. Subsequently, a product after incubation was subjected to bisulfite treatment by adding 300 μL of 10 M sodium hydrogen sulfite solution thereto and incubating the resulting mixture at 80° C. for 40 minutes. Thereafter, a nucleic acid contained in the resulting product was purified with a nucleic acid purification kit (manufactured by QIAGEN under the trade name of Qiaquick PCR purification kit). Sodium hydroxide was added to the resulting nucleic acid so as to have a final concentration of 0.3 M, and the resulting mixture was incubated at room temperature for 5 minutes. The resulting product was purified with a spin column for nucleic acid purification (manufactured by GE Healthcare under the trade name of MicroSpin S-300 HR Columns), to give analysis samples of Preparation Examples 6 to 8.

Example 3

Figure 7:
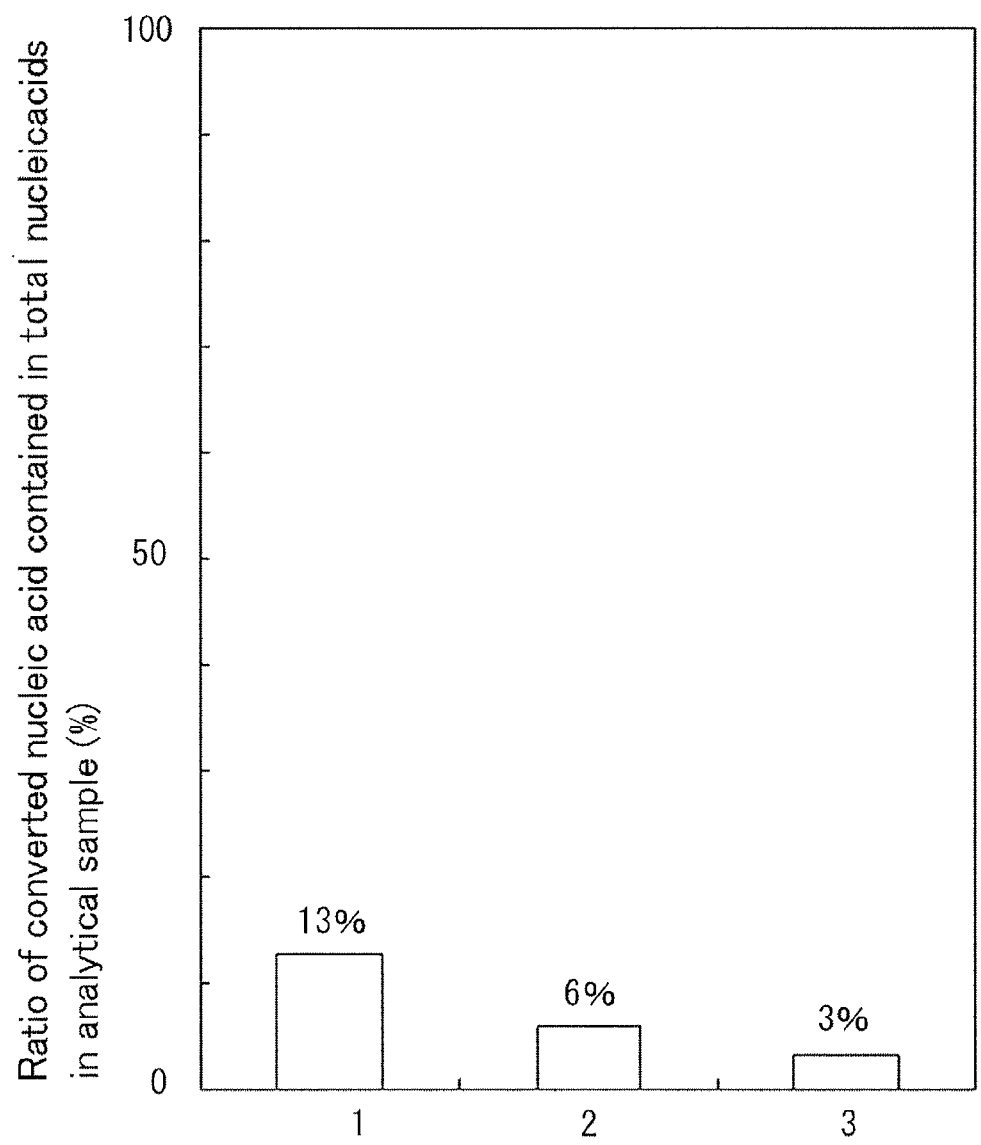
FIG. 7 is a graph showing the result of calculating the ratio of converted nucleic acid contained in total nucleic acids in an analysis sample in Example 3.

The ratio of a converted nucleic acid contained in total nucleic acids in each analysis sample was calculated by carrying the same operations as those in Example 1 with the kit for determination of unmethylated cytosine conversion treatment of Experimental Example 2 except that any one of the analytical samples of Preparation Examples 6 to 8 was used in place of the analytical sample 1 or the analytical sample 2 in Example 1. The results are shown in FIG. 7. In FIG. 7, bar 1 shows the result of a case where the analysis sample of Preparation Example 6 was used. Bar 2 shows the result of a case where the analysis sample of Preparation Example 7 was used. Bar 3 shows the result of a case where the analysis sample of Preparation Example 8 was used.

From the results shown in FIG. 7, it was revealed that, by the kit for determination of unmethylated cytosine conversion treatment of Experimental Example 2, for not only a cell-derived DNA sample, but also a breast cancer tissue-derived DNA sample, the ratio of a converted nucleic acid contained in total nucleic acids in the sample after bisulfite treatment can be obtained.

As described above, it was revealed that, by using the kit for determination of unmethylated cytosine conversion treatment of Experimental Example 2, the ratio of a converted nucleic acid contained in total nucleic acids in the sample after bisulfite treatment can be obtained, regardless of the type of the biological sample and the method of bisulfite treatment. From these results, it is suggested that, even in the case of various unmethylated cytosine conversion treatments, whether or not the unmethylated cytosine conversion treatment is properly carried out can be determined based on the ratio of a converted nucleic acid contained in total nucleic acids in the analytical sample.

SEQUENCE LISTING FREE TEXT

SEQ ID NO: 1 is a sequence of a primer.
SEQ ID NO: 2 is a sequence of a primer.
SEQ ID NO: 3 is a sequence of a primer.
SEQ ID NO: 4 is a sequence of a primer.
SEQ ID NO: 5 is a sequence of a primer.
SEQ ID NO: 6 is a sequence of a primer.
SEQ ID NO: 7 is a target sequence.
SEQ ID NO: 8 is a sequence of the standard DNA.
SEQ ID NO: 9 is a sequence of the standard DNA corresponding to a primer set 1 for checking an amount of a nucleic acid.
SEQ ID NO: 10 is a sequence of the standard DNA corresponding to a primer set 1 for checking a conversion treatment.

The invention claimed is:

1. A method for determining whether or not an unmethylated cytosine conversion treatment that converts unmethylated cytosine into a base other than cytosine is properly carried out, comprising the steps of:
   (A) converting unmethylated cytosine of the biological DNA contained in a sample into a base other than cytosine, to give an unmethylated cytosine conversion sample;
   (B) carrying out nucleic acid amplification reactions of the following (i) and (ii):
      (i) a nucleic acid amplification reaction using the unmethylated cytosine conversion sample obtained in the step (A) and a first primer set comprising a primer that hybridizes with a nucleic acid comprising a nucleotide sequence not containing cytosine in the nucleotide sequence of the biological DNA and
      (ii) a nucleic acid amplification reaction using the unmethylated cytosine conversion sample obtained in the step (A) and a second primer set comprising plural primers that hybridize with a nucleic acid comprising a nucleotide sequence in which cytosine in a nucleotide sequence containing cytosine and not containing a CpG site is converted into a base other than cytosine in the nucleotide sequence of the biological DNA;
   (C) determining the amount of the amplification product obtained in the nucleic acid amplification reaction (i) and the amount of the amplification product obtained in the nucleic acid amplification reaction (ii) of the step (B);
   (D) calculating the ratio of the amount of the amplification product obtained in the nucleic acid amplification reaction (ii) to the amount of the amplification product obtained in the nucleic acid amplification reaction (i); and
   (E) determining whether or not the step (A) is properly carried out, based on the calculation result obtained in the step (D),
   wherein the nucleotide sequence not containing cytosine and the nucleotide sequence containing cytosine and not containing a CpG site are in a same chromosome of the biological body, and
   wherein the nucleotide sequence not containing cytosine and the nucleotide sequence containing cytosine and not containing a CpG site are contained in a nucleotide sequence of 300 bp or less in the nucleotide sequence of the biological DNA,
   wherein the biological DNA contains tumor cell DNA.

2. A method for analyzing methylated DNA comprising the steps of:
   (A) converting unmethylated cytosine of biological DNA contained in a sample into a base other than cytosine, to give an unmethylated cytosine conversion sample;
   (B) carrying out nucleic acid amplification reactions of the following (i) and (ii):
      (i) a nucleic acid amplification reaction using the unmethylated cytosine conversion sample obtained in the step (A) and a first primer set comprising a primer that hybridizes with a nucleic acid comprising a nucleotide sequence not containing cytosine in the nucleotide sequence of the biological DNA and
      (ii) a nucleic acid amplification reaction using the unmethylated cytosine conversion sample obtained in the step (A) and a second primer set comprising plural primers that hybridize with a nucleic acid comprising a nucleotide sequence in which cytosine in a nucleotide sequence containing cytosine and not containing a CpG site is converted into a base other than cytosine in the nucleotide sequence of the biological DNA;
   (C) determining the amount of the amplification product obtained in the nucleic acid amplification reaction (i) and the amount of the amplification product obtained in the nucleic acid amplification reaction (ii) of the step (B);
   (D) calculating the ratio of the amount of the amplification product obtained in the nucleic acid amplification reaction (ii) to the amount of the amplification product obtained in the nucleic acid amplification reaction (i);
   (E) determining whether or not the step (A) is properly carried out, based on the calculation result obtained in the step (D), and
   (F) analyzing methylated DNA using the unmethylated cytosine conversion sample obtained in the step (A), when the step (A) is determined as properly carried out in the step (E),
   wherein the nucleotide sequence not containing cytosine and the nucleotide sequence containing cytosine and not containing a CpG site are in the same chromosome of the biological body, and
   wherein the nucleotide sequence not containing cytosine and the nucleotide sequence containing cytosine and not containing a CpG site are contained in a nucleotide sequence of 300 bp or less in the nucleotide sequence of the biological DNA,
   wherein the biological DNA contains tumor cell DNA.

3. The method according to claim 1, wherein at least one primer contained in the first primer set is a primer that hybridizes with a nucleic acid amplified by nucleic acid amplification using the second primer set.

4. The method according to claim 1, wherein at least one primer contained in the second primer set hybridizes with a nucleic acid comprising a nucleotide sequence in which cytosine is converted into a base other than cytosine, wherein the nucleic acid comprising the nucleotide sequence is amplified by the first primer.

5. The method according to claim 1, wherein the unmethylated cytosine conversion treatment is a treatment of DNA with bisulfite.

6. The method according to claim 1, wherein the base other than cytosine is uracil.

7. The method according to claim 1, wherein the biological DNA is human genomic DNA.

8. The method according to claim 1, wherein the first primer set is a primer set comprising a primer comprising a nucleotide sequence as shown in SEQ ID NO: 1 and a primer comprising a nucleotide sequence as shown in SEQ ID NO: 2.

9. The method according to claim 1, wherein the second primer set is a primer set comprising a primer comprising a nucleotide sequence as shown in SEQ ID NO: 3 and a primer comprising a nucleotide sequence as shown in SEQ ID NO: 4.

10. The method according to claim 1, wherein the step (E) comprises comparing the calculated ratio with a predetermined threshold value, and whether or not the step (A) is properly carried out is determined based on the comparison result.

11. The method according to claim 10, wherein in the step (E) it is determined that the step (A) is properly carried out when the ratio is higher than or equal to the predetermined threshold value.

12. A method for determining whether or not an unmethylated cytosine conversion treatment that converts unmethylated cytosine into a base other than cytosine is properly carried out, comprising the steps of:
(A) converting unmethylated cytosine of a biological DNA contained in a sample into a base other than cytosine, to give an unmethylated cytosine conversion sample;
(B) carrying out nucleic acid amplification reactions of the following (i) and (ii):
  (i) a nucleic acid amplification reaction using the unmethylated cytosine conversion sample obtained in the step (A) and a first primer set comprising a primer that hybridizes with a nucleic acid comprising a nucleotide sequence not containing cytosine in the nucleotide sequence of the biological DNA, and
  (ii) a nucleic acid amplification reaction using the unmethylated cytosine conversion sample obtained in the step (A) and a second primer set comprising plural primers that hybridize with a nucleic acid comprising a nucleotide sequence in which cytosine in a nucleotide sequence containing cytosine and not containing a CpG site is converted into a base other than cytosine in the nucleotide sequence of the biological DNA;
(C) determining the amount of the amplification product obtained in the nucleic acid amplification reaction (i) and the amount of the amplification product obtained in the nucleic acid amplification reaction (ii) of the step (B);
(D) calculating the ratio of the amount of the amplification product obtained in the nucleic acid amplification reaction (ii) to the amount of the amplification product obtained in the nucleic acid amplification reaction (i); and
(E) determining whether or not the step (A) is properly carried out, based on the calculation result obtained in the step (D);
wherein an overlapping region in the biological DNA exists between a nucleic acid amplified by the first primer set and a nucleic acid amplified by the second primer set.

13. The method according to claim 12, wherein nucleotide sequence not containing cytosine and the nucleotide sequence containing cytosine and not containing a CpG site are contained in a nucleotide sequence of 300 bp or less in the nucleotide sequence of the biological DNA.

14. The method according to claim 12, wherein the step (E) comprises comparing the calculated ratio with a predetermined threshold value, and whether or not the step (A) is properly carried out is determined based on the comparison result.

15. The method according to claim 12, wherein in the step (E) it is determined that the step (A) is properly carried out when the ratio is higher than or equal to the predetermined threshold value.

* * * * *